US010233471B2

(12) United States Patent
Li et al.

(10) Patent No.: US 10,233,471 B2
(45) Date of Patent: Mar. 19, 2019

(54) METHODS OF PRECONDITIONING PRETREATED CELLULOSIC MATERIAL

(71) Applicant: Novozymes A/S, Bagsvaerd (DK)

(72) Inventors: Xin Li, Raleigh, NC (US); Brandon Emme, Kansas City, MO (US); Lorraine Putnam, Youngsville, NC (US); Mads Torry Smith, Raleigh, NC (US)

(73) Assignee: Novozyme A/S, Bagsvaerd (DK)

( * ) Notice: Subject to any disclaimer, the term of this patent is extended or adjusted under 35 U.S.C. 154(b) by 10 days.

(21) Appl. No.: 14/891,186

(22) PCT Filed: May 15, 2014

(86) PCT No.: PCT/US2014/038181
§ 371 (c)(1),
(2) Date: Nov. 13, 2015

(87) PCT Pub. No.: WO2014/186565
PCT Pub. Date: Nov. 20, 2014

(65) Prior Publication Data
US 2016/0115510 A1 Apr. 28, 2016

Related U.S. Application Data

(60) Provisional application No. 61/824,082, filed on May 16, 2013.

(51) Int. Cl.
C12P 19/14 (2006.01)
C12N 9/02 (2006.01)
C12P 19/02 (2006.01)
C11B 1/02 (2006.01)
C13K 1/02 (2006.01)
C12N 9/34 (2006.01)
C11B 1/10 (2006.01)
C12P 7/14 (2006.01)
C12P 7/16 (2006.01)
C12P 7/64 (2006.01)

(52) U.S. Cl.
CPC ............ C12P 19/14 (2013.01); C11B 1/025 (2013.01); C11B 1/10 (2013.01); C12N 9/0061 (2013.01); C12N 9/2428 (2013.01); C12P 7/14 (2013.01); C12P 7/16 (2013.01); C12P 7/64 (2013.01); C12P 19/02 (2013.01); C12Y 110/03002 (2013.01); C12Y 302/01003 (2013.01); C13K 1/02 (2013.01); C12P 2201/00 (2013.01); C12P 2203/00 (2013.01)

(58) Field of Classification Search
None
See application file for complete search history.

(56) References Cited

U.S. PATENT DOCUMENTS

| 5,843,499 A | 12/1998 | Moreau | |
|---|---|---|---|
| 8,163,976 B2 | 4/2012 | Tien et al. | |
| 2008/0131947 A1 | 6/2008 | Wicking | |
| 2009/0311752 A1 | 12/2009 | Bodie | |
| 2010/0159509 A1 | 6/2010 | Xu | |
| 2010/0273227 A1* | 10/2010 | Jin | C12P 7/10 435/155 |
| 2011/0136176 A1* | 6/2011 | Shimoda | C08H 8/00 435/72 |
| 2012/0028299 A1* | 2/2012 | Li | C12N 1/22 435/41 |
| 2012/0094358 A1 | 4/2012 | Medoff | |
| 2012/0159839 A1 | 6/2012 | Koskinen et al. | |
| 2012/0196332 A1 | 8/2012 | Muniglia | |
| 2012/0276593 A1 | 11/2012 | Li | |

FOREIGN PATENT DOCUMENTS

| WO | 2001/60182 A1 | 8/2001 |
|---|---|---|
| WO | 2008134259 A1 | 11/2008 |
| WO | 2013016115 A1 | 1/2013 |

OTHER PUBLICATIONS

Ximenes et al, 2010, Enzyme Microb Technol, vol. 46, No. 3-4, pp. 170-176.

* cited by examiner

Primary Examiner — Yong D Pak
(74) Attorney, Agent, or Firm — David Fazzolare

(57) ABSTRACT

The invention relates to methods of preconditioning pretreated cellulosic material in the presence of a combination of phenol oxidizing enzyme and glucoamylase. The invention also relates to processes of producing sugars and fermentation products including a preconditioning step. Finally the invention relates to a composition suitable for preconditioning.

12 Claims, 3 Drawing Sheets
Specification includes a Sequence Listing.

SEQUENCE LISTING

```
<160> NUMBER OF SEQ ID NOS: 13

<210> SEQ ID NO 1
<211> LENGTH: 797
<212> TYPE: PRT
<213> ORGANISM: Trichoderma reesei

<400> SEQUENCE: 1
```

```
Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
                20                  25                  30

Gly Gln Pro Asp Leu Tyr Pro Glu Thr Leu Ala Thr Leu Thr Leu Ser
            35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65              70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
    115                 120                 125

Ala Thr Ser Phe Pro Met Pro Ile Leu Thr Thr Ala Ala Leu Asn Arg
130             135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
    195                 200                 205

Gly Ile Gln Gly Gly Val Asp Pro Glu His Leu Lys Val Ala Ala Thr
210             215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270

Leu Met Cys Ala Tyr Asn Ser Val Asn Gly Val Pro Ser Cys Ala Asn
    275                 280                 285

Ser Phe Phe Leu Gln Thr Leu Leu Arg Glu Ser Trp Gly Phe Pro Glu
290             295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
    355                 360                 365

Ser Val Thr Arg Leu Tyr Ala Asn Leu Val Arg Leu Gly Tyr Phe Asp
370             375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415
```

Leu Lys Asn Asp Gly Thr Leu Pro Leu Ser Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
                485                 490                 495

Asp Ala Ile Ile Tyr Leu Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Leu Lys Ser Asn Lys Lys Val
545                 550                 555                 560

Asn Ser Leu Val Trp Gly Gly Tyr Pro Gly Gln Ser Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Glu Val Thr Ile Glu Asn Trp Pro
    770                 775                 780

Leu Glu Glu Gln Gln Ile Lys Asp Ala Thr Pro Asp Ala
785                 790                 795

<210> SEQ ID NO 2
<211> LENGTH: 452
<212> TYPE: PRT
<213> ORGANISM: Thielavia terrestris

<400> SEQUENCE: 2

```
Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
                100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
        130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
                180                 185                 190

Phe Pro Gly Ala Tyr Ser Ala Thr Asp Pro Gly Ile Leu Ile Asn Ile
                195                 200                 205

Tyr Tyr Pro Val Pro Thr Ser Tyr Gln Asn Pro Gly Pro Ala Val Phe
        210                 215                 220

Ser Cys Met Leu Ala Asn Gly Ala Ile Val Phe Leu Ala Ala Ala Leu
225                 230                 235                 240

Gly Val Ser Gly His Tyr Thr Trp Pro Arg Val Asn Asp Gly Ala Asp
                245                 250                 255

Trp Gln Gln Val Arg Lys Ala Asp Asn Trp Gln Asp Asn Gly Tyr Val
        260                 265                 270

Gly Asp Val Thr Ser Pro Gln Ile Arg Cys Phe Gln Ala Thr Pro Ser
        275                 280                 285

Pro Ala Pro Ser Val Leu Asn Thr Thr Ala Gly Ser Thr Val Thr Tyr
290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
                325                 330                 335

Ala Val Trp Phe Lys Val Tyr Glu Asp His Pro Thr Phe Gly Ala Gln
                340                 345                 350

Leu Thr Trp Pro Ser Thr Gly Lys Ser Ser Phe Ala Val Pro Ile Pro
            355                 360                 365

Pro Cys Ile Lys Ser Gly Tyr Tyr Leu Leu Arg Ala Glu Gln Ile Gly
        370                 375                 380

Leu His Val Ala Gln Ser Val Gly Gly Ala Gln Phe Tyr Ile Ser Cys
385                 390                 395                 400

Ala Gln Leu Ser Val Thr Gly Gly Gly Ser Thr Glu Pro Pro Asn Lys
                405                 410                 415
```

-continued

```
Val Ala Phe Pro Gly Ala Tyr Ser Ala Thr Asp Pro Gly Ile Leu Ile
                420                 425                 430

Asn Ile Tyr Tyr Pro Val Pro Thr Ser Tyr Gln Asn Pro Gly Pro Ala
            435                 440                 445

Val Phe Ser Cys
    450

<210> SEQ ID NO 3
<211> LENGTH: 326
<212> TYPE: PRT
<213> ORGANISM: Aspergillus fumigatus

<400> SEQUENCE: 3

Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
                20                  25                  30

Tyr Gly Ser Gln Cys Val Arg Leu Pro Ala Ser Asn Ser Pro Val Thr
            35                  40                  45

Asn Val Ala Ser Asp Asp Ile Arg Cys Asn Val Gly Thr Ser Arg Pro
        50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325
```

<210> SEQ ID NO 4
<211> LENGTH: 250
<212> TYPE: PRT
<213> ORGANISM: Thermoascus aurantiacus

<400> SEQUENCE: 4

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 5
<211> LENGTH: 863
<212> TYPE: PRT
<213> ORGANISM: Aspergillus fumigatus

<400> SEQUENCE: 5

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

```
Pro Arg Leu Gly Ile Asn Trp Gly Leu Cys Gly Gln Asp Ser Pro Leu
                85                  90                  95
Gly Ile Arg Phe Ser Asp Leu Asn Ser Ala Phe Pro Ala Gly Thr Asn
            100                 105                 110
Val Ala Ala Thr Trp Asp Lys Thr Leu Ala Tyr Leu Arg Gly Lys Ala
        115                 120                 125
Met Gly Glu Glu Phe Asn Asp Lys Gly Val Asp Ile Leu Leu Gly Pro
    130                 135                 140
Ala Ala Gly Pro Leu Gly Lys Tyr Pro Asp Gly Arg Ile Trp Glu
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
            180                 185                 190
Ile Leu Asn Glu Gln Glu His Phe Arg Gln Val Gly Glu Ala Gln Gly
        195                 200                 205
Tyr Gly Tyr Asn Ile Thr Glu Thr Ile Ser Ser Asn Val Asp Asp Lys
    210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
            260                 265                 270
Gly Phe Gln Gly Phe Val Met Ser Asp Trp Ser Ala His His Ser Gly
        275                 280                 285
Val Gly Ala Ala Leu Ala Gly Leu Asp Met Ser Met Pro Gly Asp Ile
    290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
            340                 345                 350
Pro Pro Asn Phe Ser Ser Trp Thr Arg Asp Glu Tyr Gly Trp Glu His
        355                 360                 365
Ser Ala Val Ser Glu Gly Ala Trp Thr Lys Val Asn Asp Phe Val Asn
    370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
            420                 425                 430
Ala Asn Gly Cys Pro Asp Arg Gly Cys Asp Asn Gly Thr Leu Ala Met
        435                 440                 445
Ala Trp Gly Ser Gly Thr Ala Asn Phe Pro Tyr Leu Val Thr Pro Glu
    450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
                485                 490                 495
```

```
Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
            530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
            610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
            850                 855                 860

<210> SEQ ID NO 6
<211> LENGTH: 406
<212> TYPE: PRT
<213> ORGANISM: Aspergillus aculeatus

<400> SEQUENCE: 6

Met Val Gly Leu Leu Ser Ile Thr Ala Ala Leu Ala Ala Thr Val Leu
1               5                   10                  15
```

Pro Asn Ile Val Ser Ala Val Gly Leu Asp Gln Ala Ala Val Ala Lys
            20                  25                  30

Gly Leu Gln Tyr Phe Gly Thr Ala Thr Asp Asn Pro Glu Leu Thr Asp
         35                  40                  45

Ile Pro Tyr Val Thr Gln Leu Asn Asn Thr Ala Asp Phe Gly Gln Ile
 50                  55                  60

Thr Pro Gly Asn Ser Met Lys Trp Asp Ala Thr Glu Pro Ser Gln Gly
 65                  70                  75                  80

Thr Phe Thr Phe Thr Lys Gly Asp Val Ile Ala Asp Leu Ala Glu Gly
                 85                  90                  95

Asn Gly Gln Tyr Leu Arg Cys His Thr Leu Val Trp Tyr Asn Gln Leu
            100                 105                 110

Pro Ser Trp Val Thr Ser Gly Thr Trp Thr Asn Ala Thr Leu Thr Ala
            115                 120                 125

Ala Leu Lys Asn His Ile Thr Asn Val Val Ser His Tyr Lys Gly Lys
130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
                180                 185                 190

Tyr Asn Asp Tyr Asn Leu Glu Tyr Gly Gly Ala Lys Ala Ala Ser Ala
            195                 200                 205

Arg Ala Ile Val Gln Leu Val Lys Asn Ala Gly Ala Lys Ile Asp Gly
            210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
            260                 265                 270

Thr Leu Ala Gln Gln Ser Ser Asp Phe Gln Ala Leu Val Gln Ser Cys
            275                 280                 285

Val Gln Thr Thr Gly Cys Val Gly Phe Thr Ile Trp Asp Trp Thr Asp
290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Thr Ala
            340                 345                 350

Thr Ala Thr Gly Lys Thr Thr Thr Thr Thr Thr Gly Ala Thr Ser Thr
            355                 360                 365

Gly Thr Thr Ala Ala His Trp Gly Gln Cys Gly Gly Leu Asn Trp Ser
            370                 375                 380

Gly Pro Thr Ala Cys Ala Thr Gly Tyr Thr Cys Thr Tyr Val Asn Asp
385                 390                 395                 400

Tyr Tyr Ser Gln Cys Leu
            405

<210> SEQ ID NO 7
<211> LENGTH: 253

<212> TYPE: PRT
<213> ORGANISM: Penicillium emersonii

<400> SEQUENCE: 7

Met Leu Ser Ser Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 8
<211> LENGTH: 397
<212> TYPE: PRT
<213> ORGANISM: Aspergillus fumigatus

<400> SEQUENCE: 8

Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

```
Leu Met Arg Cys His Thr Leu Val Trp His Ser Gln Leu Pro Asn Trp
                100                 105                 110

Val Ser Ser Gly Ser Trp Thr Asn Ala Thr Leu Leu Ala Ala Met Lys
            115                 120                 125

Asn His Ile Thr Asn Val Val Thr His Tyr Lys Gly Lys Cys Tyr Ala
        130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Ala Cys Val Ser Thr
        275                 280                 285

Thr Gly Cys Val Gly Val Thr Ile Trp Asp Trp Thr Asp Lys Tyr Ser
290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
370                 375                 380

Thr Cys Gln Lys Leu Asn Asp Trp Tyr Ser Gln Cys Leu
385                 390                 395

<210> SEQ ID NO 9
<211> LENGTH: 792
<212> TYPE: PRT
<213> ORGANISM: Aspergillus fumigatus

<400> SEQUENCE: 9

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
        35                  40                  45

Phe Pro Asp Cys Glu Asn Gly Pro Leu Ser Lys Thr Leu Val Cys Asp
    50                  55                  60

Thr Ser Ala Arg Pro His Asp Arg Ala Ala Ala Leu Val Ser Met Phe
65                  70                  75                  80
```

```
Thr Phe Glu Glu Leu Val Asn Thr Gly Asn Thr Ser Pro Gly Val
                85                  90                  95

Pro Arg Leu Gly Leu Pro Pro Tyr Gln Val Trp Ser Glu Ala Leu His
        100                 105                 110

Gly Leu Asp Arg Ala Asn Phe Thr Asn Glu Gly Glu Tyr Ser Trp Ala
    115                 120                 125

Thr Ser Phe Pro Met Pro Ile Leu Thr Met Ser Ala Leu Asn Arg Thr
130                 135                 140

Leu Ile Asn Gln Ile Ala Thr Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
                195                 200                 205

Ile Gln Gly Gly Val Asp Pro Glu His Leu Lys Leu Val Ala Thr Ala
    210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
                260                 265                 270

Met Cys Ser Tyr Asn Ala Val Asn Gly Val Pro Ser Cys Ala Asn Ser
            275                 280                 285

Phe Phe Leu Gln Thr Leu Leu Arg Asp Thr Phe Gly Phe Val Glu Asp
290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Asp Ser Ile Arg
                325                 330                 335

Ala Gly Thr Asp Ile Asp Cys Gly Thr Thr Tyr Gln Tyr Tyr Phe Gly
                340                 345                 350

Glu Ala Phe Asp Glu Gln Glu Val Thr Arg Ala Glu Ile Glu Arg Gly
        355                 360                 365

Val Ile Arg Leu Tyr Ser Asn Leu Val Arg Leu Gly Tyr Phe Asp Gly
        370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
        420                 425                 430

Ala Leu Ile Gly Pro Trp Met Asn Val Thr Thr Gln Leu Gln Gly Asn
        435                 440                 445

Tyr Phe Gly Pro Ala Pro Tyr Leu Ile Ser Pro Leu Asn Ala Phe Gln
    450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495
```

```
Asp Val Ile Ile Phe Ala Gly Gly Ile Asp Asn Thr Leu Glu Ala Glu
                500                 505                 510

Ala Met Asp Arg Met Asn Ile Thr Trp Pro Gly Asn Gln Leu Gln Leu
            515                 520                 525

Ile Asp Gln Leu Ser Gln Leu Gly Lys Pro Leu Ile Val Leu Gln Met
        530                 535                 540

Gly Gly Gly Gln Val Asp Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
            580                 585                 590

Val Thr Gln Tyr Pro Ala Glu Tyr Ala Thr Gln Phe Pro Ala Thr Asp
        595                 600                 605

Met Ser Leu Arg Pro His Gly Asn Asn Pro Gly Gln Thr Tyr Met Trp
    610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
            660                 665                 670

Glu Gln Met Pro Leu Leu Asn Phe Thr Val Thr Ile Thr Asn Thr Gly
        675                 680                 685

Lys Val Ala Ser Asp Tyr Thr Ala Met Leu Phe Ala Asn Thr Thr Ala
690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
            740                 745                 750

Pro Gly Lys Tyr Glu Leu Ala Leu Asn Asn Glu Arg Ser Val Val Leu
        755                 760                 765

Gln Phe Val Leu Thr Gly Arg Glu Ala Val Ile Phe Lys Trp Pro Val
    770                 775                 780

Glu Gln Gln Gln Ile Ser Ser Ala
785                 790

<210> SEQ ID NO 10
<211> LENGTH: 532
<212> TYPE: PRT
<213> ORGANISM: Aspergillus fumigatus

<400> SEQUENCE: 10

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80
```

```
Thr Trp Asp Thr Thr Ile Cys Pro Asp Asp Ala Thr Cys Ala Ser Asn
                    85              90              95

Cys Ala Leu Glu Gly Ala Asn Tyr Glu Ser Thr Tyr Gly Val Thr Ala
            100             105             110

Ser Gly Asn Ser Leu Arg Leu Asn Phe Val Thr Thr Ser Gln Gln Lys
            115             120             125

Asn Ile Gly Ser Arg Leu Tyr Met Met Lys Asp Asp Ser Thr Tyr Glu
130             135             140

Met Phe Lys Leu Leu Asn Gln Glu Phe Thr Phe Asp Val Asp Val Ser
145             150             155             160

Asn Leu Pro Cys Gly Leu Asn Gly Ala Leu Tyr Phe Val Ala Met Asp
                165             170             175

Ala Asp Gly Gly Met Ser Lys Tyr Pro Thr Asn Lys Ala Gly Ala Lys
            180             185             190

Tyr Gly Thr Gly Tyr Cys Asp Ser Gln Cys Pro Arg Asp Leu Lys Phe
            195             200             205

Ile Asn Gly Gln Ala Asn Val Glu Gly Trp Gln Pro Ser Ser Asn Asp
210             215             220

Ala Asn Ala Gly Thr Gly Asn His Gly Ser Cys Cys Ala Glu Met Asp
225             230             235             240

Ile Trp Glu Ala Asn Ser Ile Ser Thr Ala Phe Thr Pro His Pro Cys
                245             250             255

Asp Thr Pro Gly Gln Val Met Cys Thr Gly Asp Ala Cys Gly Gly Thr
            260             265             270

Tyr Ser Ser Asp Arg Tyr Gly Gly Thr Cys Asp Pro Asp Gly Cys Asp
            275             280             285

Phe Asn Ser Phe Arg Gln Gly Asn Lys Thr Phe Tyr Gly Pro Gly Met
290             295             300

Thr Val Asp Thr Lys Ser Lys Phe Thr Val Val Thr Gln Phe Ile Thr
305             310             315             320

Asp Asp Gly Thr Ser Ser Gly Thr Leu Lys Glu Ile Lys Arg Phe Tyr
                325             330             335

Val Gln Asn Gly Lys Val Ile Pro Asn Ser Glu Ser Thr Trp Thr Gly
            340             345             350

Val Ser Gly Asn Ser Ile Thr Thr Glu Tyr Cys Thr Ala Gln Lys Ser
            355             360             365

Leu Phe Gln Asp Gln Asn Val Phe Glu Lys His Gly Gly Leu Glu Gly
370             375             380

Met Gly Ala Ala Leu Ala Gln Gly Met Val Leu Val Met Ser Leu Trp
385             390             395             400

Asp Asp His Ser Ala Asn Met Leu Trp Leu Asp Ser Asn Tyr Pro Thr
                405             410             415

Thr Ala Ser Ser Thr Thr Pro Gly Val Ala Arg Gly Thr Cys Asp Ile
            420             425             430

Ser Ser Gly Val Pro Ala Asp Val Glu Ala Asn His Pro Asp Ala Tyr
            435             440             445

Val Val Tyr Ser Asn Ile Lys Val Gly Pro Ile Gly Ser Thr Phe Asn
450             455             460

Ser Gly Gly Ser Asn Pro Gly Gly Gly Thr Thr Thr Thr Thr Thr Thr
465             470             475             480

Gln Pro Thr Thr Thr Thr Thr Ala Gly Asn Pro Gly Gly Thr Gly
            485             490             495
```

Val Ala Gln His Tyr Gly Gln Cys Gly Ile Gly Trp Thr Gly Pro
                500                 505                 510

Thr Thr Cys Ala Ser Pro Tyr Thr Cys Gln Lys Leu Asn Asp Tyr Tyr
            515                 520                 525

Ser Gln Cys Leu
        530

<210> SEQ ID NO 11
<211> LENGTH: 454
<212> TYPE: PRT
<213> ORGANISM: Aspergillus fumigatus

<400> SEQUENCE: 11

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
                20                  25                  30

Ser Gly Pro Thr Ser Cys Val Ala Gly Ala Ala Cys Ser Thr Leu Asn
            35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Ser Ala Pro Thr Val Thr Ala Ser
                85                  90                  95

Gly Asn Pro Phe Ser Gly Tyr Gln Leu Tyr Ala Asn Pro Tyr Tyr Ser
                100                 105                 110

Ser Glu Val His Thr Leu Ala Met Pro Ser Leu Pro Ser Ser Leu Gln
            115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
    195                 200                 205

Asp Ala Ile Arg Ala Gln Leu Val Lys Tyr Ser Asp Val His Thr Ile
210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
    275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

```
Lys Tyr Ile Asn Ala Met Ala Pro Leu Leu Lys Glu Ala Gly Phe Asp
                340                 345                 350

Ala His Phe Ile Met Asp Thr Ser Arg Asn Gly Val Gln Pro Thr Lys
            355                 360                 365

Gln Asn Ala Trp Gly Asp Trp Cys Asn Val Ile Gly Thr Gly Phe Gly
        370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
                420                 425                 430

Pro Glu Ala Gly Thr Trp Phe Gln Ala Tyr Phe Glu Gln Leu Leu Thr
            435                 440                 445

Asn Ala Asn Pro Ser Phe
    450

<210> SEQ ID NO 12
<211> LENGTH: 620
<212> TYPE: PRT
<213> ORGANISM: Myceliophthora thermophila

<400> SEQUENCE: 12

Met Lys Ser Phe Ile Ser Ala Ala Thr Leu Leu Val Gly Ile Leu Thr
1               5                   10                  15

Pro Ser Val Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
                35                  40                  45

Gln Ser Cys Asn Thr Pro Ser Asn Arg Ala Cys Trp Thr Asp Gly Tyr
        50                  55                  60

Asp Ile Asn Thr Asp Tyr Glu Val Asp Ser Pro Asp Thr Gly Val Val
65                  70                  75                  80

Arg Pro Tyr Thr Leu Thr Leu Thr Glu Val Asp Asn Trp Thr Gly Pro
                85                  90                  95

Asp Gly Val Val Lys Glu Lys Val Met Leu Val Asn Ser Ile Ile
            100                 105                 110

Gly Pro Thr Ile Phe Ala Asp Trp Gly Asp Thr Ile Gln Val Thr Val
        115                 120                 125

Ile Asn Asn Leu Glu Thr Asn Gly Thr Ser Ile His Trp His Gly Leu
130                 135                 140

His Gln Lys Gly Thr Asn Leu His Asp Gly Ala Asn Gly Ile Thr Glu
145                 150                 155                 160

Cys Pro Ile Pro Pro Lys Gly Gly Arg Lys Val Tyr Arg Phe Lys Ala
                165                 170                 175

Gln Gln Tyr Gly Thr Ser Trp Tyr His Ser His Phe Ser Ala Gln Tyr
            180                 185                 190

Gly Asn Gly Val Val Gly Ala Ile Gln Ile Asn Gly Pro Ala Ser Leu
        195                 200                 205

Pro Tyr Asp Thr Asp Leu Gly Val Phe Pro Ile Ser Asp Tyr Tyr Tyr
    210                 215                 220

Ser Ser Ala Asp Glu Leu Val Glu Leu Thr Lys Asn Ser Gly Ala Pro
225                 230                 235                 240

Phe Ser Asp Asn Val Leu Phe Asn Gly Thr Ala Lys His Pro Glu Thr
```

245                 250                 255
Gly Glu Gly Glu Tyr Ala Asn Val Thr Leu Thr Pro Gly Arg Arg His
            260                 265                 270

Arg Leu Arg Leu Ile Asn Thr Ser Val Glu Asn His Phe Gln Val Ser
        275                 280                 285

Leu Val Asn His Thr Met Cys Ile Ile Ala Ala Asp Met Val Pro Val
    290                 295                 300

Asn Ala Met Thr Val Asp Ser Leu Phe Leu Gly Val Gly Gln Arg Tyr
305                 310                 315                 320

Asp Val Val Ile Glu Ala Asn Arg Thr Pro Gly Asn Tyr Trp Phe Asn
                325                 330                 335

Val Thr Phe Gly Gly Gly Leu Leu Cys Gly Gly Ser Arg Asn Pro Tyr
            340                 345                 350

Pro Ala Ala Ile Phe His Tyr Ala Gly Ala Pro Gly Gly Pro Pro Thr
        355                 360                 365

Asp Glu Gly Lys Ala Pro Val Asp His Asn Cys Leu Asp Leu Pro Asn
    370                 375                 380

Leu Lys Pro Val Val Ala Arg Asp Val Pro Leu Ser Gly Phe Ala Lys
385                 390                 395                 400

Arg Ala Asp Asn Thr Leu Asp Val Thr Leu Asp Thr Thr Gly Thr Pro
                405                 410                 415

Leu Phe Val Trp Lys Val Asn Gly Ser Ala Ile Asn Ile Asp Trp Gly
            420                 425                 430

Arg Ala Val Val Asp Tyr Val Leu Thr Gln Asn Thr Ser Phe Pro Pro
        435                 440                 445

Gly Tyr Asn Ile Val Glu Val Asn Gly Ala Asp Gln Trp Ser Tyr Trp
    450                 455                 460

Leu Ile Glu Asn Asp Pro Gly Ala Pro Phe Thr Leu Pro His Pro Met
465                 470                 475                 480

His Leu His Gly His Asp Phe Tyr Val Leu Gly Arg Ser Pro Asp Glu
                485                 490                 495

Ser Pro Ala Ser Asn Glu Arg His Val Phe Asp Pro Ala Arg Asp Ala
            500                 505                 510

Gly Leu Leu Ser Gly Ala Asn Pro Val Arg Arg Asp Val Ser Met Leu
        515                 520                 525

Pro Ala Phe Gly Trp Val Val Leu Ser Phe Arg Ala Asp Asn Pro Gly
    530                 535                 540

Ala Trp Leu Phe His Cys His Ile Ala Trp His Val Ser Gly Gly Leu
545                 550                 555                 560

Gly Val Val Tyr Leu Glu Arg Ala Asp Asp Leu Arg Gly Ala Val Ser
                565                 570                 575

Asp Ala Asp Ala Asp Leu Asp Arg Leu Cys Ala Asp Trp Arg Arg
            580                 585                 590

Tyr Trp Pro Thr Asn Pro Tyr Pro Lys Ser Asp Ser Gly Leu Lys His
        595                 600                 605

Arg Trp Val Glu Glu Gly Glu Trp Leu Val Lys Ala
    610                 615                 620

<210> SEQ ID NO 13
<211> LENGTH: 640
<212> TYPE: PRT
<213> ORGANISM: Aspergillus niger
<220> FEATURE:
<221> NAME/KEY: SIGNAL
<222> LOCATION: (1)..(18)

```
<220> FEATURE:
<221> NAME/KEY: mat_peptide
<222> LOCATION: (19)..(640)

<400> SEQUENCE: 13

Met Ser Phe Arg Ser Leu Leu Ala Leu Ser Gly Leu Val Cys Thr Gly
            -15                 -10                  -5

Leu Ala Asn Val Ile Ser Lys Arg Ala Thr Leu Asp Ser Trp Leu Ser
    -1  1               5                  10

Asn Glu Ala Thr Val Ala Arg Thr Ala Ile Leu Asn Asn Ile Gly Ala
 15                  20                  25                  30

Asp Gly Ala Trp Val Ser Gly Ala Asp Ser Gly Ile Val Val Ala Ser
                 35                  40                  45

Pro Ser Thr Asp Asn Pro Asp Tyr Phe Tyr Thr Trp Thr Arg Asp Ser
             50                  55                  60

Gly Leu Val Leu Lys Thr Leu Val Asp Leu Phe Arg Asn Gly Asp Thr
         65                  70                  75

Ser Leu Leu Ser Thr Ile Glu Asn Tyr Ile Ser Ala Gln Ala Ile Val
         80                  85                  90

Gln Gly Ile Ser Asn Pro Ser Gly Asp Leu Ser Ser Gly Ala Gly Leu
 95                 100                 105                 110

Gly Glu Pro Lys Phe Asn Val Asp Glu Thr Ala Tyr Thr Gly Ser Trp
                115                 120                 125

Gly Arg Pro Gln Arg Asp Gly Pro Ala Leu Arg Ala Thr Ala Met Ile
                130                 135                 140

Gly Phe Gly Gln Trp Leu Leu Asp Asn Gly Tyr Thr Ser Thr Ala Thr
                145                 150                 155

Asp Ile Val Trp Pro Leu Val Arg Asn Asp Leu Ser Tyr Val Ala Gln
            160                 165                 170

Tyr Trp Asn Gln Thr Gly Tyr Asp Leu Trp Glu Glu Val Asn Gly Ser
175                 180                 185                 190

Ser Phe Phe Thr Ile Ala Val Gln His Arg Ala Leu Val Glu Gly Ser
                195                 200                 205

Ala Phe Ala Thr Ala Val Gly Ser Ser Cys Ser Trp Cys Asp Ser Gln
                210                 215                 220

Ala Pro Glu Ile Leu Cys Tyr Leu Gln Ser Phe Trp Thr Gly Ser Phe
            225                 230                 235

Ile Leu Ala Asn Phe Asp Ser Ser Arg Ser Gly Lys Asp Ala Asn Thr
            240                 245                 250

Leu Leu Gly Ser Ile His Thr Phe Asp Pro Glu Ala Ala Cys Asp Asp
255                 260                 265                 270

Ser Thr Phe Gln Pro Cys Ser Pro Arg Ala Leu Ala Asn His Lys Glu
                275                 280                 285

Val Val Asp Ser Phe Arg Ser Ile Tyr Thr Leu Asn Asp Gly Leu Ser
                290                 295                 300

Asp Ser Glu Ala Val Ala Val Gly Arg Tyr Pro Glu Asp Thr Tyr Tyr
            305                 310                 315

Asn Gly Asn Pro Trp Phe Leu Cys Thr Leu Ala Ala Ala Glu Gln Leu
            320                 325                 330

Tyr Asp Ala Leu Tyr Gln Trp Asp Lys Gln Gly Ser Leu Glu Val Thr
335                 340                 345                 350

Asp Val Ser Leu Asp Phe Phe Lys Ala Leu Tyr Ser Asp Ala Ala Thr
                355                 360                 365

Gly Thr Tyr Ser Ser Ser Ser Ser Thr Tyr Ser Ser Ile Val Asp Ala
```

-continued

```
                   370                 375                 380
Val Lys Thr Phe Ala Asp Gly Phe Val Ser Ile Val Glu Thr His Ala
        385                 390                 395

Ala Ser Asn Gly Ser Met Ser Glu Gln Tyr Asp Lys Ser Asp Gly Glu
400                     405                 410

Gln Leu Ser Ala Arg Asp Leu Thr Trp Ser Tyr Ala Ala Leu Leu Thr
415                 420                 425                 430

Ala Asn Asn Arg Arg Asn Ser Val Val Pro Ala Ser Trp Gly Glu Thr
                435                 440                 445

Ser Ala Ser Ser Val Pro Gly Thr Cys Ala Ala Thr Ser Ala Ile Gly
            450                 455                 460

Thr Tyr Ser Ser Val Thr Val Thr Ser Trp Pro Ser Ile Val Ala Thr
        465                 470                 475

Gly Gly Thr Thr Thr Thr Ala Thr Pro Thr Gly Ser Gly Ser Val Thr
    480                 485                 490

Ser Thr Ser Lys Thr Thr Ala Thr Ala Ser Lys Thr Ser Thr Ser Thr
495                 500                 505                 510

Ser Ser Thr Ser Cys Thr Thr Pro Thr Ala Val Ala Val Thr Phe Asp
                515                 520                 525

Leu Thr Ala Thr Thr Thr Tyr Gly Glu Asn Ile Tyr Leu Val Gly Ser
            530                 535                 540

Ile Ser Gln Leu Gly Asp Trp Glu Thr Ser Asp Gly Ile Ala Leu Ser
        545                 550                 555

Ala Asp Lys Tyr Thr Ser Ser Asp Pro Leu Trp Tyr Val Thr Val Thr
    560                 565                 570

Leu Pro Ala Gly Glu Ser Phe Glu Tyr Lys Phe Ile Arg Ile Glu Ser
575                 580                 585                 590

Asp Asp Ser Val Glu Trp Glu Ser Asp Pro Asn Arg Glu Tyr Thr Val
                595                 600                 605

Pro Gln Ala Cys Gly Thr Ser Thr Ala Thr Val Thr Asp Thr Trp Arg
            610                 615                 620
```

METHODS OF PRECONDITIONING PRETREATED CELLULOSIC MATERIAL

CROSS-REFERENCE TO RELATED APPLICATIONS

This application is a 35 U.S.C. 371 national application of PCT/US2014/038181 filed May 15, 2014 and published as WO2014/186565 on Nov. 20, 2014, which claims priority or the benefit under 35 U.S.C. 119 of U.S. provisional application no. US 61/824,082 filed May 16, 2013 the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to methods of preconditioning pretreated cellulolytic material and the impact of preconditioning on oil recovery/extraction, fermentation product production and sugar production processes.

BACKGROUND

Cellulosic materials are available in sufficient quantities as a low-cost feedstock for fuel ethanol production. Cellulosic materials, including corn fiber and sorghum, contain oil. Methods of extracting oil from, e.g., corn fiber are well known in the art.

U.S. Pat. No. 5,843,499 concerns a method of preparing corn fiber oil by separating corn fiber from corn kernels, drying the corn fiber, grinding the corn fiber, extracting oil from the ground corn fiber by means of an organic solvent and supercritical fluid extraction, and separating the extracted corn fiber oil from the organic solvent.

It is an object of the present invention to provide improved methods of preconditioning pretreated cellulosic material and to provide improved processes of recovering/extracting oil, producing fermentation products and sugars from pretreated lignocellulosic materials.

SUMMARY

Described herein are methods of preconditioning pretreated cellulosic material to improve enzymatic saccharification (hydrolysis). Described are also processes of recovering oil from preconditioned (oil-containing) cellulolytic material. Also concerned are processes of producing a fermentation product, such as ethanol, or sugars from lignocellulose-containing material. Compositions suitable for use in methods and/or processes of the invention are also described.

In the first aspect the invention relates to methods of preconditioning pretreated cellulosic material comprising incubating the pretreated cellulosic material with phenol oxidizing enzyme and glucoamylase.

In a preferred embodiment the phenol oxidizing enzyme is a laccase, such as one from *Myceliophthora thermophila* (MtL) (WO 95/33836), such as the laccase shown in SEQ ID NO: 12 herein. In an embodiment the glucoamylase is derived from a strain of *Aspergillus*, such *Aspergillus niger* (e.g., the one in SEQ ID NO: 13) or *Aspergillus oryzae*.

In an embodiment a beta-glucosidase is present or added during preconditioning. The beta-glucosidase may be derived from a strain of *Aspergillus*, such as *Aspergillus niger*, *Aspergillus fumigatus*, or *Aspergillus oryzae*.

In an embodiment an alpha-amylase is present or added during preconditioning. In an embodiment the alpha-amylase is derived from a strain of *Aspergillus*, such as *Aspergillus niger* or *Aspergillus oryzae*.

In an embodiment an enzyme preparation comprising glucoamylase, beta-glucosidase and alpha-amylase is present or added during preconditioning. In an embodiment this enzyme preparation is derived from a strain of *Aspergillus*, such as *Aspergillus niger*. In a specific embodiment the enzyme preparation is Glucoamylase 188 (see Materials & Methods"-section).

In an embodiment a hemicellulase, such as a hemicellulolytic enzyme preparation, such as Hemicellulolytic Enzyme Preparation H3 (see "Materials & Methods"-section), is present or added during preconditioning.

The cellulosic material may be any cellulosic material, such as the materials in the "Cellulosic Materials"-section below. In a preferred embodiment the cellulosic material is corn fiber, which may be dilute acid pretreated or autohydrolyzed. In an embodiment the cellulosic material is oil seeds.

In an embodiment the pretreated cellulosic material is unwashed. In an embodiment the pretreated cellulosic material is un-detoxified. In an embodiment the cellulosic material is washed, undetoxified or unwashed pretreated corn fiber, corn stover (PCS), corn cob, wheat straw, rice straw and/or switch grass.

In an embodiment preconditioning occurs at 5-50% TS (Total Solids), such as 10-40% TS, such as 15-35% TS. In an embodiment preconditioning incubation occurs for at least 30 minutes, e.g., at least 1 hour, at least 2 hours, at least 4 hours, at least 8 hours, at least 12 hours, or at least 24 hours, such as from 30 minutes to 24 hours. In an embodiment preconditioning incubation occurs at a temperature between 20-70° C., such as between 40-60° C. According to the invention an increased amount of oil is released and may be recovered, after a saccharification of the preconditioned cellulolytic material, compared to when no preconditioning is done.

In a second aspect, the invention relates to processes of recovering oil from pretreated cellulosic material comprising:

(i) preconditioning the cellulosic material with a phenol oxidizing enzyme;

(ii) saccharifying the preconditioned material with a cellulolytic enzyme preparation;

(iii) recovering oil from saccharified material in step (ii).

In a preferred embodiment the phenol oxidizing enzyme is a laccase, such as one from *Myceliophthora thermophila* (MtL) (WO 95/33836), such as the laccase shown in SEQ ID NO: 12 herein. In an embodiment preconditioning step (i) is carried out in accordance with the preconditioning method of the invention.

In an embodiment the cellulolytic enzyme preparation used for saccharification in step (ii) is of fungal origin, such as derived from *Trichoderma* (e.g., *Trichoderma reesei*). The cellulolytic enzyme preparation may also be derived from other fungi as described in the "Cellulolytic Enzyme Preparation:-section below.

A hemicellulase may also be present or added during saccharification. In an embodiment saccharification step (ii) is carried out in the presence a cellulolytic enzyme preparation including enzyme activities selected from the group of endoglucanase, cellobiohydrolase, and beta-glucosidase (e.g., *Aspergillus fumigatus* beta-glucosidase, such as the one shown in SEQ ID NO: 5 herein, or *Aspergillus oryzae* beta-glucosidase). In an embodiment saccharification step (ii) is carried out in the present of a polypeptide having cellulolytic enhancing activity, such as GH61 polypeptide, e.g., a *Thermoascus aurantiacus* GH61 polypeptide, such as the one shown in SEQ ID NO: 4 herein or *Penicillium emersonii* GH61 polypeptide, such as the one shown in SEQ ID NO: 7 herein. In an embodiment saccharification step (ii) is carried out in the presence of one or more enzymes selected from hemicellulase, expansin, esterase, laccase, ligninolytic enzyme, pectinase, peroxidase, protease, and swollenin.

In an embodiment the hemicellulase may be selected from the group of xylanases (e.g., an *Aspergillus aculeatus*, such as the one shown in SEQ ID NO: 6 herein, or *Aspergillus fumigatus* xylanase, such as the one shown in SEQ ID NO: 8 herein, and a xylosidase (e.g., *Aspergillus fumigatus* beta-xylosidase, such as the one shown in SEQ ID NO: 9 herein.

In a preferred embodiment the cellulolytic enzyme preparation, present or added during saccharification, is a cellulolytic enzyme preparation derived from *Trichoderma reesei*, further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140 or SEQ ID NO: 11 herein. Further, the cellulolytic enzyme preparation may further be supplemented with 10% hemicellulolytic enzyme preparation comprising a cellulolytic enzyme preparation from *Trichoderma reesei* further comprising *Aspergillus fumigatus* xylanase (SEQ ID NO: 8 herein) and *Aspergillus fumigatus* beta-xylosidase (SEQ ID NO: 9 herein).

A process of the invention results in an increased amount of oil being released compared to when no preconditioning is done.

In a third aspect the invention relates to processes of producing a fermentation product from cellulosic material comprising:

(a) preconditioning the cellulosic material with a phenol oxidizing enzyme;

(b) saccharifying the preconditioned material with a cellulolytic enzyme preparation;

(c) fermenting the saccharified material with a fermenting organism (d) optionally recovering oil from saccharified material in step (b) and/or the fermented material in step (c).

In an embodiment the phenol oxidizing enzyme is a laccase, such as one from *Myceliophthora thermophila* (MtL) (WO 95/33836), such as the laccase shown in SEQ ID NO: 12 herein. In an embodiment preconditioning step (a) is carried out in accordance with the invention. In an embodiment the fermentation product is recovered after fermentation in step (c). According to the invention saccharification step (b) and fermentation step (c) may be carried out as separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC).

In an embodiment the cellulolytic enzyme preparation present or added during saccharification is of fungal origin. In a preferred embodiment the cellulolytic enzyme preparation is derived from *Trichoderma* (e.g., *Trichoderma reesei*).

In an embodiment saccharification step (b) is carried out in the presence a cellulolytic enzyme preparation including enzyme activities selected from the group of endoglucanase, cellobiohydrolase, and beta-glucosidase (e.g., *Aspergillus fumigatus* beta-glucosidase, such as the one shown in SEQ ID NO: 5 herein, or *Aspergillus oryzae* beta-glucosidase).

In an embodiment saccharification is carried out in the presence of a polypeptide having cellulolytic enhancing activity (e.g., a *Thermoascus aurantiacus* GH61 polypeptide, such as the one shown in SEQ ID NO: 4 herein, or *Penicillium emersonii* GH61 polypeptide, such as the one shown in SEQ ID NO: 7 herein).

In an embodiment saccharification step (b) is carried out in the presence of one or more enzymes selected from hemicellulase, expansin, esterase, laccase, ligninolytic enzyme, pectinase, peroxidase, protease, and swollenin.

In an embodiment the hemicellulase is selected from a xylanase (e.g., an *Aspergillus aculeatus* xylanase, such as the one shown in SEQ ID NO: 6 herein, or *Aspergillus fumigatus* xylanase, such as the one shown in SEQ ID NO: 8 herein), and a xylosidase (e.g., *Aspergillus fumigatus* beta-xylosidase, such as the one shown in SEQ ID NO: 9 herein).

In an embodiment the fermentation product is an alcohol (e.g., ethanol or butanol), an organic acid, a ketone, an amino acid, or a gas. In a preferred embodiment the fermentation product is ethanol. A process of the invention may result in an increased saccharification rate compared to when no preconditioning is done. Also a process of the invention results in an increased amount of oil being released compared to when no preconditioning is done.

In a preferred embodiment the cellulolytic enzyme preparation, present or added during saccharification, is a cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140. Further, the cellulolytic enzyme preparation may further be supplemented with 10% hemicellulase enzyme composition derived from *Trichoderma reesei* further comprising *Aspergillus fumigatus* xylanase III (SEQ ID NO: 8 herein) and *Aspergillus fumigatus* beta-xylosidase (SEQ ID NO: 9 herein). In an aspect the invention relates to processes of producing sugars from pretreated cellulosic material comprising:

(i) preconditioning said cellulosic material with a phenol oxidizing enzyme;

(ii) saccharifying the conditioned material with a cellulolytic enzyme preparation;

(iii) optionally recovering/extracting oil from saccharified material in step (ii).

In a preferred embodiment the phenol oxidizing enzyme is a laccase, such as one from *Myceliophthora thermophile* (MtL) (WO 95/33836), such as the one shown in SEQ ID NO: 12 herein.

In an embodiment preconditioning in step (i) is carried out in accordance with a preconditioning method of the invention. In an embodiment the process further comprises recovering sugars from the saccharified material from step (ii).

According to the invention sugars obtained or recovered according to the invention may be used in processes, e.g., for producing syrups (e.g., High Fructose Corn Syrups) and lignocellulose-derived plastics (e.g., polyethylene, polystyrene, and polypropylene), polylactic acid (e.g., for producing PET).

In an embodiment the cellulolytic enzyme preparation is of fungal origin. In a preferred embodiment the cellulolytic enzyme preparation is derived from *Trichoderma* (e.g., *Trichoderma reesei*). In an embodiment saccharification step (ii) is carried out in the presence of a cellulolytic enzyme preparation comprising enzyme activities selected from the group of endoglucanase, cellobiohydrolase, and beta-glucosidase (e.g., *Aspergillus fumigatus* beta-glucosidase, such as the one disclosed in SEQ ID NO: 5 herein; or *Aspergillus oryzae* beta-glucosidase).

In an embodiment saccharification step (ii) is carried out in the presence of a polypeptide having cellulolytic enhancing activity (e.g., a *Thermoascus aurantiacus* GH61 polypeptide, such as the one shown in SEQ ID NO: 4 herein, or *Penicillium emersonii* GH61 polypeptide, such as the one shown in SEQ ID NO: 7 herein).

In an embodiment saccharification step (ii) is carried out using one or more enzymes selected from hemicellulase, expansin, esterase, laccase, ligninolytic enzyme, pectinase, peroxidase, protease, and swollenin.

In an embodiment the hemicellulase is selected from a xylanase (e.g., an *Aspergillus aculeatus* xylanase, such as the one shown in SEQ ID NO: 6 herein, or *Aspergillus fumigatus* xylanase, such as the one shown in SEQ ID NO: 8 herein), an acetylxylan esterase, a feruloyl esterase, an arabinofuranosidase, a xylosidase (e.g., *Aspergillus fumigatus* beta-xylosidase, such as the one shown in SEQ ID NO: 9), and a glucuronidase.

In a preferred embodiment the cellulolytic enzyme preparation, present or added during saccharification, is a cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140. Further, the cellulolytic enzyme preparation may further be supplemented with 10% hemicellulase enzyme composition derived from *Trichoderma reesei* further comprising *Aspergillus fumigatus* xylanase III (SEQ ID NO: 8 herein) and *Aspergillus fumigatus* beta-xylosidase (SEQ ID NO: 9 herein).

In a final aspect the invention relates to compositions comprising a phenol oxidizing enzyme and a glucoamylase. In an embodiment the phenol oxidizing enzyme is a laccase, such as one from *Myceliophthora thermophila* (MtL) (WO 95/33836), such as the one shown in SEQ ID NO: 12.

In an embodiment the composition comprises glucoamylase derived from a strain of *Aspergillus*, such as *Aspergillus niger* or *Aspergillus oryzae*.

In an embodiment the composition further comprises a beta-glucosidase. In an embodiment, the beta-glucosidase is derived from a strain of *Aspergillus*, such as *Aspergillus niger*, *Aspergillus fumigatus*, or *Aspergillus oryzae*. In an embodiment the composition comprises an alpha-amylase. In an embodiment the alpha-amylase is derived from a strain of *Aspergillus*, such as *Aspergillus niger* or *Aspergillus oryzae*.

In an embodiment the composition of the invention further comprises a hemicellulase.

In a preferred embodiment the hemicellulase is a xylanase and/or a beta-xylosidase. In an embodiment the xylanase is derived from *Aspergillus*, such as *Aspergillus fumigatus*, such as the one shown in SEQ ID NO: 8 herein; or *Aspergillus aculeatus*, such as the one shown in SEQ ID NO: 6 herein. In an embodiment the beta-xylosidase is derived from *Aspergillus*, such as *Aspergillus fumigatus*, such as the one shown in SEQ ID NO: 9 herein.

Definitions

Enzymes:

Cellulolytic enzyme preparation, cellulolytic composition, or cellulase: The term "cellulolytic enzyme preparation", "cellulolytic composition", or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

Cellulolytic enzyme activity is determined by measuring the increase in hydrolysis of a cellulosic material by cellulolytic enzyme(s) under the following conditions: 1-50 mg of cellulolytic enzyme protein/g of cellulose in Pretreated Corn Stover ("PCS") (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5 L (Novozymes NS, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptide having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose.

For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Cellobiohydrolase: The term "cellobiohydrolase" ("CBH") means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178).

Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Endoglucanase: The term "endoglucanase" ("EG") means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components.

Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Hemicellulolytic enzyme, hemicellulolytic enzyme preparation or hemicellulase: The term "hemicellulolytic enzyme", "hemicellulolytic enzyme preparation" or "hemicellulase" means one or more (e.g., several) enzymes that hydrolyze a hemicellulosic material. See, for example, Shallom, D. and Shoham, Y. Microbial hemicellulases. Current Opinion In Microbiology, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure & Appl. Chem. 59: 1739-1752, at a suitable temperature, e.g., 50° C., 55° C., or 60° C., and pH, e.g., 5.0 or 5.5.

Alpha-Amylases (alpha-1,4-glucan-4-glucanohydrolases, EC 3.2.1.1) are a group of enzymes, which catalyze the hydrolysis of starch and other linear and branched 1,4-glucosidic oligo- and polysaccharides.

Glucoamylases (glucan 1,4-alpha-glucosidase, EC 3.2.1.3) are a group of enzymes, which catalyze the hydrolysis of terminal (1→4)-linked alpha-D-glucose residues successively from non-reducing ends of the chains with release of beta-D-glucose.

Other Definitions

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix. Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Mature polypeptide: The term "mature polypeptide" means a polypeptide in its final form following translation and any post-translational modifications, such as N-terminal processing, C-terminal truncation, glycosylation, phosphorylation, etc. For instance, the mature polypeptide of an *A. fumigatus* cellobiohydrolase I is amino acids 27 to 532 of SEQ ID NO: 10 herein based on the SignalP program (Nielsen et al., 1997, *Protein Engineering* 10: 1-6) that predicts amino acids 1 to 26 of SEQ ID NO: 10 herein are a signal peptide. In another aspect, the mature polypeptide of an *A. fumigates* cellobiohydrolase II is amino acids 20 to 454 of SEQ ID NO: 11 herein based on the SignalP program that predicts amino acids 1 to 19 of SEQ ID NO: 11 herein are a signal peptide. In another aspect, the mature polypeptide of an *A. fumigatus* beta-glucosidase is amino acids 20 to 863 of SEQ ID NO: 5 herein based on the SignalP program that predicts amino acids 1 to 19 of SEQ ID NO: 5 herein are a signal peptide. In another aspect, the mature polypeptide of a *Penicillium* sp. GH61 polypeptide is amino acids 26 to 253 of SEQ ID NO: 7 herein based on the SignalP program that predicts amino acids 1 to 25 of SEQ ID NO: 7 herein are a signal peptide.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity.

Parent Enzyme: The term "parent" means an enzyme to which an alteration is made to produce a variant. The parent may be a naturally occurring (wild-type) polypeptide or a variant thereof.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 85%, e.g., at least 90% or at least 95% of the nucleotides of the mature polypeptide coding sequence of an enzyme.

Variant: The term "variant" means a polypeptide having enzyme or enzyme enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Wild-Type Enzyme: The term "wild-type" enzyme means an enzyme expressed by a naturally occurring microorganism, such as a bacterium, yeast, or filamentous fungus found in nature.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION

Figure 1:
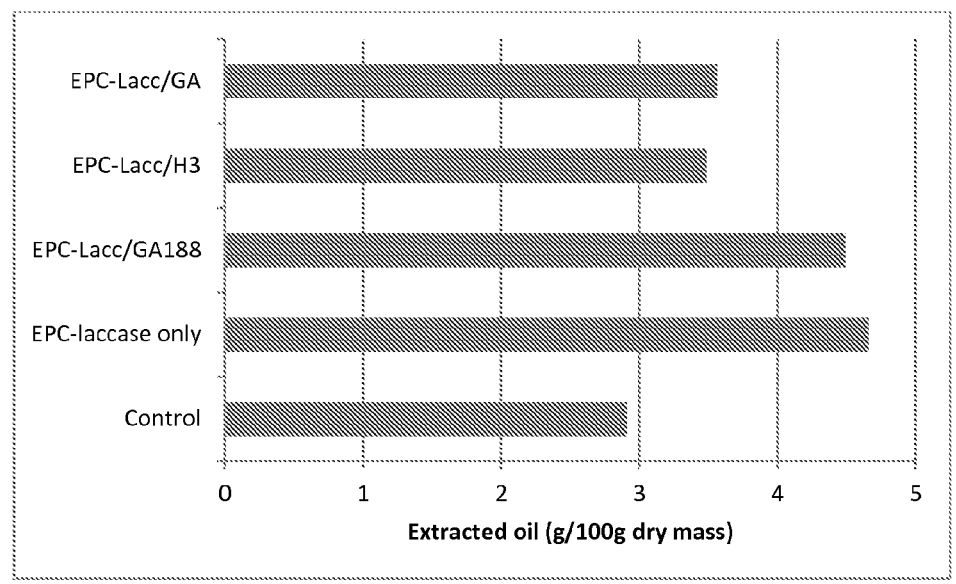
FIG. 1 shows the effect of enzymatic preconditioning on oil extraction/recovery from corn fiber hydrolysate.
Control: saccharification with Cellulolytic Enzyme Preparation C3;
EPC-Laccase only: preconditioned with Laccase A only and then hydrolyzed with Cellulolytic Enzyme Preparation C3;
EPC-Lacc H3: preconditioned with Laccase A and Hemicellulolytic Enzyme Preparation H3 and then hydrolyzed with Cellulolytic Enzyme Preparation C3;
EPC-Lacc/GA188: preconditioned with Laccase A and Glucoamylase 188 and then hydrolyzed with Cellulolytic Enzyme Preparation C3.
EPC-Lacc/GA: preconditioned with Laccase A and Glucoamylase GA and then hydrolyzed with Cellulolytic Enzyme Preparation C3.

Described herein are methods of preconditioning pretreated cellulosic material to improve enzymatic saccharification (hydrolysis). Described are also processes of recovering oil from preconditioned (oil-containing) cellulolytic material. Also concerned are processes of producing a fermentation product, such as ethanol, or sugars from lignocellulose-containing material. Compositions suitable for use in methods and/or processes of the invention are also described.

The present inventors have surprisingly found that enzymatic preconditioning of dilute acid pretreated oil-contained corn fiber material with a combination of laccase and glucoamylase before saccharifying (i.e., hydrolyzing) with a cellulolytic enzyme preparation results in increased oil recovery after saccharification compared to when no preconditioning is done. Further, it was also found that an increased saccharification rate may be obtained compared to when no preconditioning is done. This is described in Example 1.

Preconditioning is carried out before saccharification (i.e., hydrolysis) in which sugars are produced. The sugars may be converted into a number of products including fermentation products (e.g., ethanol or butanol) or into syrups (e.g., High Fructose Corn Syrup (HFCS) and lignocellulose-derived plastics including polyethylene, polystyrene, polypropylene). Other end products include lactic acid which can serve as a feedstock for production of polylactic acid (PLA) to replace petrochemical packaging materials such as PET.

Methods of Preconditioning Pretreated Cellulosic Material

In the first aspect the invention relates to methods of preconditioning pretreated cellulosic material, comprising incubating the pretreated cellulosic material with phenol oxidizing enzyme and glucoamylase.

The phenol oxidizing enzyme may belong to any of the following EC classes including: Laccase (EC 1.10.3.2), Catechol oxidase (EC 1.10.3.1), o-Aminophenol oxidase (1.10.3.4); and Monophenol monooxygenase (1.14.18.1). In a preferred embodiment the phenol oxidizing enzyme is a laccase, such as one from *Myceliophthora thermophila* (MtL), such as the one shown in SEQ ID NO: 12 herein. In an embodiment the laccase has at least 60%, at least 70% at least 80%, at least 85%, at least 90%, at least 95%, at least 97%, at least 98%, at least 99% sequence identity to the *Myceliopthora thermophila* laccase disclosed in WO 95/33836 or SEQ ID NO: 12. Other suitable laccases are mentioned in the "Laccases"-section below. In an embodiment the phenol oxidizing enzyme, especially laccase, loading is between 1-500 µg, such as 5-100 µg EP/g cellulose. In an embodiment the laccase loading is between 0.005 and 20 mg Enzyme Protein (EP)/g cellulose, such as 0.1-1 mg EP/g cellulose.

In an embodiment the glucoamylase is derived from a strain of *Aspergillus*, such *Aspergillus niger* (e.g., the one shown in SEQ ID NO: 13 herein) or *Aspergillus oryzae*.

In an embodiment the glucoamylase has at least 60% at least 70%, at least 75%, at least 80%, at least 85%, at least 90%, at least 95%, at least 96%, at least 97%, at least 98%, at least 99% or even 100% sequence identity to the mature sequences shown in SEQ ID NO: 13 herein.

In an embodiment the glucoamylase loading is between 0.01 and 20 mg EP/g cellulose, such as 0.1-1 mg EP/g cellulose. Other suitable glucoamylases are mentioned in the "glucoamylases"-section below.

In an embodiment a beta-glucosidase is present or added during preconditioning. The beta-glucosidase may be derived from a strain of *Aspergillus*, such as *Aspergillus niger, Aspergillus fumigatus*, or *Aspergillus oryzae*. In an embodiment the beta-glycosidase loading is between 0.01 and 20 mg EP/g cellulose, such as 0.1-1 mg EP/g cellulose. Other suitable beta-glucosidases are mentioned in the "beta-glucosidase"-section below.

In an embodiment an alpha-amylase is present or added during preconditioning. In an embodiment the alpha-amylase is derived from a strain of *Aspergillus*, such as *Aspergillus niger* or *Aspergillus oryzae*. In an embodiment the alpha-amylase loading is between 0.001 and 20 mg EP/g cellulose, such as 0.01-1 mg EP/g cellulose. Other suitable alpha-amylases are mentioned in the "Alpha-Amylase"-section below.

In an embodiment a hemicellulase, such as a hemicellu-loytic enzyme preparation, such as Hemicellulolytic Enzyme Preparation H3 (see Examples), is present or added during preconditioning.

In an embodiment the hemicellulase is a hemicellulolytic enzyme preparation. In a preferred embodiment the hemi-cellulolytic enzyme preparation comprising a cellulolytic enzyme preparation from *Trichoderma reesei*, further comprising *Aspergillus fumigatus* xylanase (SEQ ID NO: 8 herein) and *Aspergillus fumigatus* beta-xylosidase (SEQ ID NO: 9 herein).

In an embodiment the hemicellulase loading is between 0.01 and 20 mg EP/g cellulose, such as 0.1-1 mg EP/g cellulose. Other suitable hemicellulases are mentioned in the "Hemicellulases"-section below.

The pretreated cellulosic material may be pretreated using any suitable method. Suitable pretreatment methods are listed in the "Pretreatment"-section below. In a preferred embodiment the pretreated cellulosic material has been dilute acid pretreated or auto-hydrolyzed before preconditioning. According to the invention the cellulosic material may be pretreated corn fiber, pretreated corn stover (PCS), pretreated corn cob, pretreated wheat straw, pretreated rice straw or pretreated switch grass. In a preferred embodiment the cellulosic material is dilute acid pretreated corn fiber. Other examples of contemplated cellulosic material can be found in the "Cellulosic Materials"-section below.

In another embodiment the pretreated cellulosic material is unwashed. In an embodiment the pretreated cellulosic material is un-detoxified. In an embodiment the cellulosic material is washed, undetoxified or unwashed pretreated corn fiber, corn stover (PCS), corn cob, wheat straw, rice straw and/or switch grass. In an embodiment preconditioning occurs at 5-50% TS (Total Solids), such as 10-40% TS, such as 15-35% TS. In an embodiment preconditioning incubating occurs for at least 30 minutes, e.g., at least 1 hour, at least 2 hours, at least 4 hours, at least 8 hours, at least 12 hours, or at least 24 hours, such as from 30 minutes to 24 hours. In an embodiment preconditioning incubation occurs at a temperature between 20-70° C., such as between 40-60° C.

A method of the invention results in an increased amount of oil being released compared to when no preconditioning is done.

Process of Extracting/Recovering Oil from Preconditioned Pretreated Cellulosic Material In a second aspect, the invention relates to processes of recovering oil from pretreated cellulosic material comprising:
(i) preconditioning the cellulosic material with a phenol oxidizing enzyme;
(ii) saccharifying the preconditioned material with a cellulolytic enzyme preparation; and
(iii) recovering oil from the saccharified material in step (ii).

In an embodiment preconditioning step (a) is carried out in accordance with a preconditioning method of the invention as described in the "Methods of Preconditioning Pretreated Cellulosic Material"-section above.

Suitable cellulosic material and methods of pretreating cellulosic materials according to the invention is described below in the "Cellulosic Materials"-section and "Pretreatment"-section, respectively.

Saccharification

In the saccharification step (i.e., hydrolysis step) the pretreated preconditioned cellulosic material is hydrolyzed to break down cellulose and/or hemicellulose to fermentable sugars, such as glucose, cellobiose, xylose, xylulose, arabinose, mannose, galactose, and/or soluble oligosaccharides. The saccharification is performed enzymatically using a cellulolytic enzyme preparation.

Saccharification (i.e., hydrolysis) may be carried out in a suitable aqueous environment under conditions that can be readily determined by one skilled in the art. In one aspect, saccharification is performed under conditions suitable for the activity of the cellulolytic enzyme preparation, preferably optimal for the cellulolytic enzyme preparation. The saccharification can be carried out as a fed batch or continuous process where the preconditioned unwashed pretreated cellulosic material (substrate) is fed gradually to the hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, e.g., about 12 to about 96 hours, about 16 to about 72 hours, or about 24 to about 48 hours. In one aspect, saccharification occurs for at least 12 hours, e.g., at least 24 hours, 36 hours, 48 hours, 60 hours, or 72 hours.

The temperature during saccharification may be in the range of about 25° C. to about 75° C., e.g., about 30° C. to about 70° C., about 35° C. to about 65° C., about 40° C. to 60° C., about 45° C. to 55° C., or about 50° C.

The pH during saccharification may be in the range of about 3.0 to 7.0, e.g., 3.5 to 6.5, 4.0 to 6.0, 4.5 to 5.5 or about 5.0.

In some aspects, the dry solids (DS) content during saccharification (e.g., total solids in the cellulosic material) is less than about 25 wt %, 20 wt %, 15 wt %, 10 wt %, 7.5 wt %, 5 wt %, 2.5 wt %, 2 wt %, 1 wt %, or 0.5 wt %.

In an embodiment sugars obtained from saccharification step (ii) may be fermentated.

In an embodiment the cellulolytic enzyme preparation used in step (ii) may be of fungal origin. In a preferred embodiment the cellulolytic enzyme preparation is derived from *Trichoderma* (e.g., *Trichoderma reesei*). In a preferred embodiment saccharification (hydrolysis) is carried out in the presence a cellulolytic enzyme preparation including enzyme activities selected from the group of endoglucanase, cellobiohydrolase, and beta-glucosidase (e.g., *Aspergillus fumigatus* or *Aspergillus oryzae* beta-glucosidase). In a preferred embodiment saccharification is carried out using a polypeptide having cellulolytic enhancing activity (e.g., a *Thermoascus aurantiacus* or *Penicillium emersonii* cellulolytic enhancing polypeptide).

In an embodiment saccharification is carried out further using one or more enzymes selected from hemicellulase, expansin, esterase, laccase, ligninolytic enzyme, pectinase, peroxidase, protease, and swollenin.

In an embodiment the hemicellulase may be a xylanase (e.g., an *Aspergillus aculeatus* or *Aspergillus fumigatus* xylanase), a xylosidase (e.g., *Aspergillus fumigatus* beta-xylosidase).

In an embodiment the fermentation product produced is an alcohol (e.g., ethanol or butanol), an organic acid, a ketone, an amino acid, or a gas.

In a preferred embodiment the phenol oxidizing enzyme is a laccase, such as one from *Myceliophthora thermophila* (MtL) (WO 95/33836), such as the laccase shown in SEQ ID NO: 12 herein. In an embodiment preconditioning step (i) is carried out in accordance with the preconditioning method of the invention.

In an embodiment the cellulolytic enzyme preparation used for saccharification in step (ii) is of fungal origin, such as derived from *Trichoderma* (e.g., *Trichoderma reesei*). A hemicellulase may also be present or added during saccharification. In an embodiment saccharification step (ii) is carried out in the presence a cellulolytic enzyme preparation including enzyme activities selected from the group of endoglucanase, cellobiohydrolase, and beta-glucosidase (e.g., *Aspergillus fumigatus* beta-glucosidase, such as the one shown in SEQ ID NO: 5 herein, or *Aspergillus oryzae* beta-glucosidase). In an embodiment saccharification step (ii) is carried out in the present of a polypeptide having cellulolytic enhancing activity, such as GH61 polypeptide, e.g., a *Thermoascus aurantiacus* GH61 polypeptide, such as the one shown in SEQ ID NO: 4 herein or *Penicillium emersonii* GH61 polypeptide, such as the one shown in SEQ ID NO: 7 herein.

In an embodiment saccharification step (ii) is carried out in the presence of one or more enzymes selected from hemicellulase, expansin, esterase, laccase, ligninolytic enzyme, pectinase, peroxidase, protease, and swollenin.

In an embodiment a hemicellulase, such as a hemicellulolytic enzyme preparation, is present or added during saccharification (and/or fermentation). In a preferred embodiment the hemicellulolytic enzyme preparation comprising a cellulolytic enzyme preparation from *Trichoderma reesei*, further comprising *Aspergillus fumigatus* xylanase (SEQ ID NO: 8 herein) and *Aspergillus fumigatus* beta-xylosidase (SEQ ID NO: 9 herein).

Examples of suitable cellulolytic enzyme preparation can be found below in the "Cellulolytic Enzyme Preparation" section.

In a preferred embodiment the cellulolytic enzyme preparation is derived from *Trichoderma* (e.g., *Trichoderma reesei*) including endoglucanase (EG), cellobiohydrolase (CBH), and beta-glucosidase (BG), and further comprises a polypeptide having cellulolytic enhancing activity (e.g., a *Thermoascus aurantiacus* or *Penicillium emersonii* cellulolytic enhancing polypeptide), beta-glucosidase (e.g., *Aspergillus fumigatus* or *Aspergillus oryzae* beta-glucosidase).

Examples of cellulolytic enzyme preparations can be found in the "Cellulolytic Enzyme Preparation"-section below.

In a preferred embodiment the cellulolytic enzyme preparation, present or added during saccharification, is a cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140. Further, the cellulolytic enzyme preparation may further be supplemented with 10% hemicellulolytic enzyme preparation comprising a cellulolytic enzyme preparation from *Trichoderma reesei* further comprising *Aspergillus fumigatus* xylanase (SEQ ID NO: 8 herein) and *Aspergillus fumigatus* beta-xylosidase (SEQ ID NO: 9 herein).

A process of the invention results in an increased amount of oil being released compared to when no preconditioning is done.

Producing Fermentation Products from Preconditioned Pretreated Cellulosic Material In a third aspect the invention relates to processes of producing a fermentation product from cellulosic material comprising:

(a) preconditioning the cellulosic material with a phenol oxidizing enzyme;

(b) saccharifying the preconditioned material with a cellulolytic enzyme preparation;

(c) fermenting the saccharified material with a fermenting organism; and (d) optionally recovering oil from the saccharified material in step (b) and/or the fermented material in step (c).

In an embodiment preconditioning step (a) is carried out in accordance with a preconditioning method of the invention as described in the "Methods of Preconditioning Pretreated Cellulosic Material"-section above.

In an embodiment saccharification step (b) is carried out as described above in the "Process of Extracting/Recovering Oil From Preconditioned Pretreated Cellulosic Material"-section.

In an embodiment the fermentation product is recovered after fermentation in step (c).

In an embodiment the cellulolytic enzyme preparation present or added during saccharification is of fungal origin.

In a preferred embodiment the cellulolytic enzyme preparation is derived from *Trichoderma* (e.g., *Trichoderma reesei*).

In an embodiment saccharification step (b) is carried out in the presence of a cellulolytic enzyme preparation including enzyme activities selected from the group of endoglucanase, cellobiohydrolase, and beta-glucosidase (e.g., *Aspergillus fumigatus* beta-glucosidase, such as the one shown in SEQ ID NO: 5 herein, or *Aspergillus oryzae* beta-glucosidase).

In an embodiment saccharification is carried out in the presence of a polypeptide having cellulolytic enhancing activity (e.g., a *Thermoascus aurantiacus* GH61 polypeptide, such as the one shown in SEQ ID NO: 4 herein, or *Penicillium emersonii* GH61 polypeptide, such as the one shown in SEQ ID NO: 7 herein).

In an embodiment saccharification step (b) is carried out in the presence of one or more enzymes selected from hemicellulase, expansin, esterase, laccase, ligninolytic enzyme, pectinase, peroxidase, protease, and swollenin.

In an embodiment the hemicellulase is selected from a xylanase (e.g., an *Aspergillus aculeatus* xylanase, such as the one shown in SEQ ID NO: 6 herein, or *Aspergillus fumigatus* xylanase, such as the one shown in SEQ ID NO: 8 herein), and a xylosidase (e.g., *Aspergillus fumigatus* beta-xylosidase, such as the one shown in SEQ ID NO: 9 herein).

In an embodiment the fermentation product is an alcohol (e.g., ethanol or butanol), an organic acid, a ketone, an amino acid, or a gas. In a preferred embodiment the fermentation product is ethanol. A process of the invention results in an increased saccharification rate compared to when no preconditioning is done. Also a process of the invention results in an increased amount of oil being released compared to when no preconditioning is done.

In an embodiment the phenol oxidizing enzyme used during preconditioning is a laccase, such as one from *Myceliophthora thermophila* (MtL) (WO 95/33836), such as the laccase shown in SEQ ID NO: 12 herein. In an embodiment a glucoamylase is present or added during preconditioning. The glucoamylase may be derived from a strain of *Aspergillus*, such *Aspergillus niger* (e.g., the one shown in SEQ ID NO: 13 herein) or *Aspergillus oryzae*. Preconditioning methods and suitable enzymes and conditions used are described above in the "Methods of Preconditioning Pretreated Cellulosic Material"-above.

In a preferred embodiment the cellulolytic enzyme preparation, present or added during saccharification, is a cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140. Further, the cellulolytic enzyme preparation may further be supplemented with 10% hemicellulase enzyme composition derived from *Trichoderma reesei* further comprising *Aspergillus fumigatus* xylanase (SEQ ID NO: 8 herein) and *Aspergillus fumigatus* beta-xylosidase (SEQ ID NO: 9 herein).

Fermentation

Sugars obtained from saccharification (hydrolysis) of the cellulosic material can be fermented by one or more (several) fermenting microorganisms capable of fermenting the sugars directly or indirectly into a desired fermentation product (e.g., ethanol).

"Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

Sugars obtained from saccharification of preconditioned pretreated cellulosic material are fermented to a product, e.g., ethanol, by a fermenting organism, such as yeast. Saccharification (hydrolysis) and fermentation can be separate or simultaneous, as described herein.

Saccharification (hydrolysis) and fermentation, separate or simultaneous, include, but are not limited to, separate saccharification (hydrolysis) and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate process steps to first saccharify (hydrolyze) cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd et al., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

Suitable fermenting organisms used according of a process of the invention is described below in the "Fermenting Organism"-section below Fermenting Organism "Fermenting organism" refers to any microorganism, including bacterial and fungal organisms, suitable for use in a fermentation process to produce a desired fermentation product. The fermenting organism can be hexose (i.e., $C_6$) and/or pentose ($C_5$) fermenting organisms, or a combination thereof. Both hexose and pentose fermenting organisms are well known in the art. Suitable fermenting organisms are able to ferment, i.e., convert, sugars, such as glucose, xylose, xylulose, arabinose, maltose, mannose, galactose, and/or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. marxianus, K. lactis, K. thermotolerans*, and *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum*, *Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Klebsiella*, such as *K. oxytoca*.

In one aspect, the yeast is a *Saccharomyces* spp. In another aspect, the yeast is *Saccharomyces cerevisiae*. In another aspect, the yeast is *Saccharomyces distaticus*. In another aspect, the yeast is *Saccharomyces uvarum*. In another aspect, the yeast is a *Kluyveromyces*. In another aspect, the yeast is *Kluyveromyces marxianus*. In another aspect, the yeast is *Kluyveromyces fragilis*. In another aspect, the yeast is a *Candida*. In another aspect, the yeast is *Candida boidinii*. In another aspect, the yeast is *Candida brassicae*. In another aspect, the yeast is *Candida diddensii*. In another aspect, the yeast is *Candida pseudotropicalis*. In another aspect, the yeast is *Candida utilis*. In another aspect, the yeast is a *Clavispora*. In another aspect, the yeast is *Clavispora lusitaniae*. In another aspect, the yeast is *Clavispora opuntiae*. In another aspect, the yeast is a *Pachysolen*. In another aspect, the yeast is *Pachysolen tannophilus*. In another aspect, the yeast is a *Pichia*. In another aspect, the yeast is a *Pichia stipitis*. In another aspect, the yeast is a *Bretannomyces*. In another aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis*, *Clostridium acetobutylicum*, *Clostridium thermocellum*, *Clostridium phytofermentans*, *Geobacillus* sp., *Thermoanaerobacter saccharolyticum*, and *Bacillus coagulans* (Philippidis, 1996, supra).

In one aspect, the bacterium is a *Zymomonas*. In one aspect, the bacterium is *Zymomonas mobilis*. In another aspect, the bacterium is a *Clostridium*. In another aspect, the bacterium is *Clostridium acetobutylicum*. In another aspect, the bacterium is *Clostridium phytofermentan*. In another aspect, the bacterium is *Clostridium thermocellum*. In another aspect, the bacterium is *Geobacillus* sp. In another aspect, the bacterium is *Thermoanaerobacter saccharolyticum*. In another aspect, the bacterium is *Bacillus coagulans*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In one aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In one aspect, the genetically modified fermenting organism is *Saccharomyces cerevisiae*. In another aspect, the genetically modified fermenting organism is *Zymomonas mobilis*. In another aspect, the genetically modified fermenting organism is *Escherichia coli*. In another aspect, the genetically modified fermenting organism is *Klebsiella oxytoca*. In another aspect, the genetically modified fermenting organism is *Kluyveromyces* sp.

It is well known in the art that the organisms described above can also be used to produce other substances, as described herein.

The fermenting organism is typically added to the degraded cellulosic material or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In one aspect, the yeast and/or another organism may be applied to the degraded cellulosic material and the fermentation is performed for about 12 hours to about 96 hours, such as 24-60 hours. In one aspect, the temperature is between about 20° C. to about 60° C., e.g., about 25° C. to about 50° C., or about 32° C. to about 50° C., and the pH is generally from about pH 3 to about pH 7, e.g., around pH 4-7, such as about pH 5. However, some fermenting organisms, e.g., bacteria, have higher fermentation temperature optima. Yeast or another microorganism is preferably applied in amounts of approximately $10^5$ to $10^{12}$, e.g., from approximately $10^7$ to $10^{10}$, especially approximately $2\times10^8$ viable cell count per mL of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry may be distilled to extract the ethanol. The ethanol obtained according to a process of the invention can be used as, e.g., fuel ethanol, drinking ethanol, i.e., potable neutral spirits, or industrial ethanol.

Fermentation Stimulators

A fermentation stimulator can be used in the processes described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the (desired) fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); and a gas (e.g., methane, hydrogen ($H_2$), carbon dioxide ($CO_2$), and carbon monoxide (CO)). The fermentation product can also be protein as a high value product.

In one aspect, the fermentation product is an alcohol. It will be understood that the term "alcohol" encompasses a substance that contains one or more hydroxyl moieties. In one aspect, the alcohol is arabinitol. In another aspect, the alcohol is butanol. In another aspect, the alcohol is ethanol. In another aspect, the alcohol is glycerol. In another aspect, the alcohol is methanol. In another aspect, the alcohol is 1,3-propanediol. In another aspect, the alcohol is sorbitol. In another aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19 (6): 595-603.

In another aspect, the fermentation product is an organic acid. In one aspect, the organic acid is acetic acid. In another aspect, the organic acid is acetonic acid. In another aspect, the organic acid is adipic acid. In another aspect, the organic acid is ascorbic acid. In another aspect, the organic acid is citric acid. In another aspect, the organic acid is 2,5-diketo-D-gluconic acid. In another aspect, the organic acid is formic acid. In another aspect, the organic acid is fumaric acid. In another aspect, the organic acid is glucaric acid. In another aspect, the organic acid is gluconic acid. In another aspect, the organic acid is glucuronic acid. In another aspect, the organic acid is glutaric acid. In another aspect, the organic acid is 3-hydroxypropionic acid. In another aspect, the organic acid is itaconic acid. In another aspect, the organic acid is lactic acid. In another aspect, the organic acid is malic acid. In another aspect, the organic acid is malonic acid. In another aspect, the organic acid is oxalic acid. In another aspect, the organic acid is propionic acid. In another aspect, the organic acid is succinic acid. In another aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

In another aspect, the fermentation product is a ketone. It will be understood that the term "ketone" encompasses a substance that contains one or more ketone moieties. In another aspect, the ketone is acetone. See, for example, Qureshi and Blaschek, 2003, supra.

In another aspect, the fermentation product is an amino acid. In one aspect, the amino acid is aspartic acid. In another aspect, the amino acid is glutamic acid. In another aspect, the amino acid is glycine. In another aspect, the amino acid is lysine. In another aspect, the amino acid is serine. In another aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another aspect, the fermentation product is an alkane. The alkane can be an unbranched or a branched alkane. In one aspect, the alkane is pentane. In another aspect, the alkane is hexane. In another aspect, the alkane is heptane. In another aspect, the alkane is octane. In another aspect, the alkane is nonane. In another aspect, the alkane is decane. In another aspect, the alkane is undecane. In another aspect, the alkane is dodecane.

In another aspect, the fermentation product is a cycloalkane. In one aspect, the cycloalkane is cyclopentane. In another aspect, the cycloalkane is cyclohexane. In another aspect, the cycloalkane is cycloheptane. In another aspect, the cycloalkane is cyclooctane.

In another aspect, the fermentation product is an alkene. The alkene can be an unbranched or a branched alkene. In one aspect, the alkene is pentene. In another aspect, the alkene is hexene. In another aspect, the alkene is heptene. In another aspect, the alkene is octene.

In one aspect, the fermentation product is isoprene. In another aspect, the fermentation product is polyketide.

In another aspect, the fermentation product is a gas. In one aspect, the gas is methane. In another aspect, the gas is $H_2$. In another aspect, the gas is $CO_2$. In another aspect, the gas is CO. See, for example, Kataoka et al., 1997, Studies on hydrogen production by continuous culture system of hydrogen-producing anaerobic bacteria, *Water Science and Technology* 36(6-7): 41-47; and Gunaseelan, 1997, *Biomass and Bioenergy*, 13(1-2): 83-114, Anaerobic digestion of biomass for methane production: A review.

Producing Sugars from Preconditioned Pretreated Cellulosic Material

In an aspect the invention relates to processes of producing sugars from pretreated cellulosic material comprising:

(i) preconditioning the cellulosic material with a phenol oxidizing enzyme;

(ii) saccharifying the conditioned material with a cellulolytic enzyme preparation;

(iii) optionally recovering oil from saccharified material in step (ii).

In a preferred embodiment the phenol oxidizing enzyme is a laccase, such as one from *Myceliophthora thermophile* (MtL) (WO 95/33836), such as the one shown in SEQ ID NO: 12 herein.

In an embodiment preconditioning in step (i) is carried out in accordance with a preconditioning method of the invention.

In an embodiment saccharification step (ii) is carried out as described above in the "Process of Extracting/Recovering Oil From Preconditioned Pretreated Cellulosic Material"-section.

In an embodiment the process further comprises recovering sugars from the saccharified material from step (ii).

According to the invention sugars obtained or recovered according to the invention may be used in processes, e.g., for producing syrups (e.g., High Fructose Corn Syrups) and lignocellulose-derived plastics (e.g., polyethylene, polystyrene, and polypropylene), polylactic acid (e.g., for producing PET).

In an embodiment the cellulolytic enzyme preparation is of fungal origin. In a preferred embodiment the cellulolytic enzyme preparation is derived from *Trichoderma* (e.g., *Trichoderma reesei*). In an embodiment saccharification step (ii) is carried out in the presence of a cellulolytic enzyme preparation comprising enzyme activities selected from the group of endoglucanase, cellobiohydrolase, and beta-glucosidase (e.g., *Aspergillus fumigatus* beta-glucosidase, such as the one disclosed in SEQ ID NO: 5 herein; or *Aspergillus oryzae* beta-glucosidase).

In an embodiment saccharification step (ii) is carried out in the presence of a polypeptide having cellulolytic enhancing activity (e.g., a *Thermoascus aurantiacus* GH61 polypeptide, such as the one shown in SEQ ID NO: 4 herein, or *Penicillium emersonii* GH61 polypeptide, such as the one shown in SEQ ID NO: 7 herein).

In an embodiment saccharification step (ii) is carried out using one or more enzymes selected from hemicellulase, expansin, esterase, laccase, ligninolytic enzyme, pectinase, peroxidase, protease, and swollenin.

In an embodiment the hemicellulase is selected from a xylanase (e.g., an *Aspergillus aculeatus* xylanase, such as the one shown in SEQ ID NO: 6 herein, or *Aspergillus fumigatus* xylanase, such as the one shown in SEQ ID NO: 8 herein), an acetylxylan esterase, a feruloyl esterase, an arabinofuranosidase, a xylosidase (e.g., *Aspergillus fumigatus* beta-xylosidase, such as the one shown in SEQ ID NO: 9), and a glucuronidase.

In a preferred embodiment the cellulolytic enzyme preparation, present or added during saccharification, is a cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140. Further, the cellulolytic enzyme preparation may further be supplemented with 10% hemicellulase enzyme composition derived from *Trichoderma reesei* further comprising *Aspergillus fumigatus* xylanase III (SEQ ID NO: 8 herein) and *Aspergillus fumigatus* beta-xylosidase (SEQ ID NO: 9 herein).

In a final aspect the invention relates to compositions comprising a phenol oxidizing enzyme and a glucoamylase. In an embodiment the phenol oxidizing enzyme is a laccase, such as one from *Myceliophthora thermophila* (MtL) (WO 95/33836), such as the one shown in SEQ ID NO: 12.

In an embodiment the composition comprises glucoamylase derived from a strain of *Aspergillus*, such as *Aspergillus niger* (e.g., the one in SEQ ID NO: 13 herein, or *Aspergillus oryzae*.

In an embodiment the composition further comprises a beta-glucosidase. In an embodiment, the beta-glucosidase is derived from a strain of *Aspergillus*, such as *Aspergillus niger*, *Aspergillus fumigatus*, or *Aspergillus oryzae*. In an embodiment the composition comprises an alpha-amylase. In an embodiment the alpha-amylase is derived from a strain of *Aspergillus*, such as *Aspergillus niger* or *Aspergillus oryzae*.

In an embodiment the composition of the invention further comprises a hemicellulase.

In a preferred embodiment the hemicellulase is a xylanase and/or a beta-xylosidase. In an embodiment the xylanase is derived from *Aspergillus*, such as *Aspergillus fumigatus*, such as the one shown in SEQ ID NO: 8 herein; or *Aspergillus aculeatus*, such as the one shown in SEQ ID NO: 6 herein. In an embodiment the beta-xylosidase is derived from *Aspergillus*, such as *Aspergillus fumigatus*, such as the one shown in SEQ ID NO: 9 herein.

A process of the invention results in a higher glucose yield compared to when no preconditioning is done.

Cellulosic Materials

As used herein, the term "cellulosic materials" refers to any lignocellulosic materials containing cellulose (a chemically homogeneous oligosaccharide or polysaccharide of beta-(1-4)-D-glucan (polymer containing beta (1-4) linked D-glucose units)). Although generally polymorphous, cellulose can be found in plant tissue primarily as an insoluble crystalline matrix of parallel glucan chains. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). Cellulosic material includes any form of cellulose, such as polysaccharides degraded or hydrolyzed to oligosaccharides. It is understood herein that the cellulose may be in the form of a component of lignocellulose, a plant cell wall material containing lignin, cellulose, and hemicellulose in a mixed matrix.

In one aspect, the cellulosic material is herbaceous material (including energy crops). In another aspect, the cellulosic material is agricultural residue. In another aspect, the cellulosic material is wood (including forestry residue). In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is wheat straw. In another aspect, the cellulosic material is bagasse. In another aspect, the cellulosic material is corn cob. In another aspect, the cellulosic material is switchgrass. In another aspect, the cellulosic material is corn fiber. In another aspect, the cellulosic material is rice straw. In another aspect, the cellulosic material is *miscanthus*. In another aspect, the cellulosic material is *arundo*. In another aspect, the cellulosic material is bamboo. In another aspect, the cellulosic material is orange peel. In another aspect, the cellulosic material is poplar. In another aspect, the cellulosic material is pine. In another aspect, the cellulosic material is aspen. In another aspect, the cellulosic material is fir. In another aspect, the cellulosic material is spuce. In another aspect, the cellulosic material is willow. In another aspect, the cellulosic material is *eucalyptus*.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

In another aspect, the cellulosic material is an aquatic biomass. As used herein the term "aquatic biomass" means biomass produced in an aquatic environment by a photosynthesis process. The aquatic biomass can be algae; submerged plants; emergent plants; and floating-leaf plants.

In a preferred embodiment the cellulosic material is oil seeds. Oils seeds include sorghum, rapeseed, soybean, palm, sunflower, cottonseed, peanut, flaxseed, linseed, safflower, palm kernel, coconut and olive.

Fiber, such as corn or wheat fiber, may be obtained by fractionation. Fractionation technologies are well-known in the art.

For instance, corn kernels are comprised of three main components: bran, endosperm, and germ. Corn bran holds the fiber, the hard outer layer of the kernel. The endosperm contains the majority of the starch, found on the interior of the kernel. The germ is at the center of the kernel by the bottom tip cap, containing an abundance of proteins and oils.

In an embodiment of the invention the cellulosic material is fiber, such as corn fiber or wheat fiber. The fiber may be obtained from a wet milling process. In another embodiment the cellulosic material is fiber obtained from wet fractionation in a dry grind process (see, e.g., Wang et al *Cereal Chem.* 82(6):734-738).

Pretreatment

Pretreated cellulosic material may be, e.g., pretreated by a chemical pretreatment, a physical pretreatment, or a chemical pretreatment and a physical pretreatment, as described below. In one aspect, the pretreated cellulosic material has been pretreated by a chemical pretreatment. In another aspect, the pretreated cellulosic material has been pretreated by physical pretreatment. In another aspect, the pretreated cellulosic material has been pretreated by a chemical pretreatment and a physical pretreatment.

Any suitable pretreatment process known in the art can be used to disrupt plant cell wall components of cellulosic material (see, e.g., Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments. In a preferred embodiment the cellulosic material (e.g., unwashed corn stover) is dilute acid pretreated.

The cellulosic material is pretreated before saccharification (hydrolysis) and/or fermentation, but after preconditioning.

Steam Pretreatment: In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment may be performed at 140-230° C., e.g., 160-200° C., or 170-190° C., where the optimal temperature range depends on any addition of a chemical catalyst. Residence time for the steam pretreatment may be 1-15 minutes, e.g., 3-12 minutes, or 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to hemicellulose monosaccharides and hemicellulose oligosaccharides, which become more solubilized. Lignin is removed to only a limited extent. The resulting liquor primarily contains dissolved hemicellulosic material (e.g., hemicellulose monosaccharides and hemicellulose oligosaccharides), whereas the remaining solids primarily consists of cellulosic material.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee at al., 1999, *Adv. Biochem. Eng. Biotechnol.* 65: 93-115). In an embodiment the pretreatment is a low severity pretreatement, such as a dilute acid pretreated carried out using 3% $H_2SO_4$ (w/w) at 160° C. for 5 minutes.

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin at al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Published Application 2002/0164730.

In one aspect, the chemical pretreatment is carried out as an acid treatment, such as a continuous dilute and/or mild acid treatment. The acid may be sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In one aspect, cellulosic material is present during pretreatment in amounts preferably between 10-80 wt %, e.g., between 20-70 wt %, or between 30-60 wt %, such as around 50 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, more preferably about 150 to about 250 psi. In another aspect, high temperature means temperatures in the range of about 100 to about 300° C., preferably about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from lignocellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Recovery

According to the invention oil may be extraction/recovered from the saccharified material (hydrolysate) and/or fermented material using any suitable well-known method in the art, e.g., using a solvent such as hexane.

According to the invention the fermentation product may optionally be recovered after fermentation using any method known in the art including, but not limited to, chromatography, electrophoretic procedures, differential solubility, distillation, or extraction. For example, alcohol is separated from the fermented material and purified by conventional methods of distillation. For instance, ethanol with a purity of up to about 96 vol. % can be obtained, which can be used as, for example, fuel ethanol, drinking ethanol, i.e., potable neutral spirits, or industrial ethanol.

Enzymes

Below sections describe polypeptides, enzymes and enzyme preparations that may be used according to the methods and processes of the invention.

Phenol Oxidizing Enzymes

A phenol oxidizing enzyme present or added during preconditioning according to the invention may be any phenol oxidizing enzyme. The phenol oxidizing enzyme may be of any origin, but preferably of fungal or bacterial origin.

The phenol oxidizing enzyme(s) may belong to any of the following EC classes including: Laccase (EC 1.10.3.2), Catechol oxidase (EC 1.10.3.1), o-Aminophenol oxidase (1.10.3.4); and Monophenol monooxygenase (1.14.18.1). Laccases are preferred.

Laccases

According to the invention a laccase may be present or added during preconditioning. Laccases (EC 1.10.3.2.) are multi-copper-containing enzymes that catalyze the oxidation of phenolic compounds. Laccases are produced by plants, bacteria and also a wide variety of fungi, including Ascomycetes such as *Aspergillus*, *Neurospora*, and *Podospora*; Deuteromycete including *Botrytis*, and Basidiomycetes such as *Collybia*, *Fomes*, *Lentinus*, *Pleurotus*, *Trametes*, and perfect forms of *Rhizoctonia*. A number of fungal laccases have been isolated. For example, Choi et al. (*Mol. Plant-Microbe Interactions* 5: 119-128, 1992) describe the molecular characterization and cloning of the gene encoding the laccase of the chestnut blight fungus, *Cryphonectria parasitica*. Kojima et al. (*J. Biol. Chem.* 265: 15224-15230, 1990; JP 2-238885) provide a description of two allelic forms of the laccase of the white-rot basidiomycete *Coriolus hirsutus*. Germann and Lerch (*Experientia* 41: 801, 1985; *PNAS USA* 83: 8854-8858, 1986) have reported the cloning and partial sequencing of the *Neurospora crassa* laccase gene. Saloheimo et al. (*J. Gen. Microbiol.* 137: 1537-1544, 1985; WO 92/01046) have disclosed a structural analysis of the laccase gene from the fungus *Phlebia radiata*.

Especially contemplated laccases include those derived from a strain of *Polyporus*, preferably *Polyporus pinsitus*; *Melanocarpus*, preferably *Melanocarpus albomyces*; *Myceliopthora*, preferably *Myceliopthora thermophila*; *Coprinus*, preferably *Coprinus cinereus*; *Rhizoctonia*, preferably *Rhizoctonia solani* or *Rhizoctonia praticola*; *Scytalidium*, preferably *Scytalidium thermophilum*; *Pyricularia*, preferably *Pyricularia oryzae*.

In an embodiment the laccase is derived from the tree *Rhus vernicifera* (Yoshida, 1883, Chemistry of Lacquer (Urushi) part 1. *J. Chem. Soc.* 43, 472-486).

In another embodiment the laccase is derived from *Polyporus pinsitus*, e.g., the one described in WO 96/00290 (Novozymes).

Jönsson et al., 1998, *Appl. Microbiol. Biotechnol.* 49, 691-697, also disclose a suitable laccase derived from *Polyporus versicolar*.

Other laccases include the one derived from *Pyricularia oryzae* concerned in, e.g., Muralikrishna et al., 1995, *Appl. Environ. Microbiol.* 61(12): 4374-4377) or the laccase disclosed in Abstract of Papers American Chemical Society vol. 209, no. 1-2, 1995 derived from a *Scytalidium thermophilum*.

The laccase may also be one derived from *Coprinus cinereus*, e.g., the one concerned in Schneider et al., 1999, *Enzyme and Microbial Technology* 25: 502-508.

Other suitable laccases include those derived from *Rhizoctonia solani* concerned in Waleithner et al., 1996, *Curr. Genet.* 29: 395-403, or derived from *Melanocarpus albomyces* concerned in Kiiskinen et al., 2004, *Microbiology* 150: 3065-3074.

Suitable bacterial laccase include those derived from *Streptomyces coelicolor*, e.g., disclosed by Machczynski et al., 2004, *Protein Science* 13: 2388-2397.

In a preferred embodiment the laccase is derived from *Myceliopthora thermophila*, e.g., the one described in WO 95/33836 (Novozymes) shown in SEQ ID NO: 12 herein.

Contemplated laccases also include those comprising an amino acid sequence having at least 60%, at least 70% at least 80%, at least 85%, at least 90%, at least 95% identity, at least 97%, at least 98%, at least 99% sequence identity to the *Myceliopthora thermophila* laccase disclosed in WO 95/33836 and SEQ ID NO: 12 herein or any of the above mentioned laccases.

Glucoamylases

According to the invention a glucoamylase may be present or added during preconditioning. A glucoamylase (glucan 1,4-α-glucosidase, EC 3.2.1.3) may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in positions A435 and S436 (Li et al., 1997, *Protein Eng.* 10: 1199-1204.

Other glucoamylases include *Athelia rolfsii* (previously denoted *Corticium rolfsfi*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces duponti, Talaromyces emersonii* (WO 99/28448), *Talaromyces leycettanus* (U.S. Pat. No. Re. 32,153), and *Talaromyces thermophilus* (U.S. Pat. No. 4,587,215).

Bacterial glucoamylases include glucoamylases from *Clostridium*, in particular *C. thermoamylolyticum* (EP 135138) and *C. thermohydrosulfuricum* (WO 86/01831), *Trametes cingulata, Pachykytospora papyracea*, and *Leucopaxillus giganteus*, all disclosed in WO 2006/069289; or *Peniophora rufomarginata* disclosed in PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may be one having a high degree of sequence identity to any of above mentioned glucoamylases, i.e., at least 60%, at least 70%, at least 75%, at least 80%, at least 85%, at least 90%, at least 95%, at least 96%, at least 97%, at least 98%, at least 99% or even 100% identity to the mature enzymes sequences shown in SEQ ID NO: 13 herein, or another glucoamylase sequence mentioned above.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™, SPIRIZYME ULTRA™, and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Glucoamylase is preferably added in a concentration between 0.01 and 20 mg EP/g cellulose, such as 0.1-1 mg EP/g cellulose.

Alpha-Amylases

According to the invention an alpha-amylase may be present or added during preconditioning. According to the invention any alpha-amylase may be used, such as of fungal, bacterial or plant origin. In a preferred embodiment the alpha-amylase is an acid alpha-amylase, e.g., acid fungal or acid bacterial alpha-amylase.

In an embodiment the alpha-amylase is an acid alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5. In an embodiment the alpha-amylase is a fungal alpha-amylase, such as an acid fungal alpha-amylase.

Fungal alpha-amylases include alpha-amylases derived from a strain of *Aspergillus*, such as, *Aspergillus kawachii, Aspergillus niger* and *Aspergillus oryzae* alpha-amylases.

A preferred acid fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain of *Aspergillus niger*. In a preferred embodiment the acid fungal alpha-amylase is an *Aspergillus niger* alpha-amylase disclosed as "AMYA_ASPNG" in the Swiss-prot/TeEMBL database under the primary accession no. P56271 and described in WO 89/01969 (Example 3—incorporated by reference). A commercially available acid fungal alpha-amylase derived from *Aspergillus niger* is SP288 (available from Novozymes NS, Denmark).

Other wild-type alpha-amylases include those derived from a strain of *Meripilus* and *Rhizomucor*, preferably a strain of *Meripilus giganteus* or *Rhizomucor pusillus* (WO 2004/055178 which is incorporated herein by reference).

In a preferred embodiment the alpha-amylase is derived from *Aspergillus kawachii* (Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL: #AB008370).

The fungal alpha-amylase may also be a wild-type enzyme comprising a starch-binding domain (SBD) and an alpha-amylase catalytic domain, or a variant thereof.

In an embodiment the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain (SBD), and optionally a linker.

Examples of hybrid alpha-amylases include those disclosed in Tables 1 to 5 of the examples in WO 2006/069290 including the variant with the catalytic domain JA118 and *Athelia rolfsii* SBD (SEQ ID NO: 100 in WO 2006/069290), *Rhizomucor pusillus* alpha-amylase with *Athelia rolfsii* AMG linker and SBD (SEQ ID NO: 101 in WO 2006/069290), *Rhizomucor pusillus* alpha-amylase with *Aspergillus niger* glucoamylase linker and SBD (which is disclosed as V039 in Table 5 in WO 2006/069290), and *Meripilus giganteus* alpha-amylase with *Athelia rolfsii* glucoamylase linker and SBD (SEQ ID NO: 102 in WO 2006/069290). Other hybrid alpha-amylases are listed in Tables 3, 4, 5, and 6 in Example 4 in WO 2006/069290 (which are hereby incorporated by reference).

Other examples of hybrid alpha-amylases include those disclosed in U.S. Patent Application Publication No. 2005/0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

Commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEX-LO™, SPEZYME™ FRED, SPEZYME™ AA, SPEZYME™ DELTA AA, GC358, GC980, and SPEZYME™ RSL (Danisco), and the acid fungal alpha-amylase sold under the trade name SP288 (available from Novozymes A/S, Denmark).

Alpha-amylase is preferably added in concentrations between 0.001 and 20 mg EP/g cellulose, such as 0.01-1 mg EP/g cellulose.

Hemicellulases

According to the invention a hemicellulase may be present or added during preconditioning or saccharification. The hemicellulase may be any hemicellulase. The hemicellulase may be in the form of a hemicellulolytic enzyme preparation. The hemicellulase may be of any origin, but preferably of fungal or bacterial origin.

The term "hemicellulase" or "hemicellulolytic enzyme" means one or more (several) enzymes that hydrolyze a hemicellulosic material. See, for example, Shallom and Shoham, 2003, Microbial hemicellulases. *Current Opinion In Microbiology*, 6(3): 219-228. Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

In an embodiment the hemicellulase present of added during preconditioning and/or saccharification is a hemicellulolytic enzyme preparation. In an embodiment the hemicellulolytic enzyme preparation is cellulolytic enzyme preparation from *Trichoderma reesei*, further comprising a xylanase and/or a beta-xylosidase. In a preferred embodiment the hemicellulolytic enzyme preparation is cellulolytic enzyme preparation from *Trichoderma reesei*, further comprising *Aspergillus fumigatus* xylanase (SEQ ID NO: 8 herein) and *Aspergillus fumigatus* beta-xylosidase (SEQ ID NO: 9 herein).

The hemicellulase or hemicellulolytic enzyme preparation may preferably be added in concentrations between 0.01 and 20 mg EP/g cellulose, such as 0.1-1 mg EP/g cellulose.

Xylanases

In a preferred embodiment the hemicellulase is a xylanase or the hemicellulolytic enzyme preparation comprises a xylanase. The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Examples of specifically contemplated xylanases include GH10 xylanases, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

The xylanase may be comprised in a cellulolytic enzyme preparation which further includes a xylanase. In one embodiment hemicellulase is a cellulolytic enzyme preparation further comprising a xylanase, preferably a GH10 xylanase, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

In an embodiment the xylanase is derived from *Aspergillus aculatues*, such as the one shown in SEQ ID NO: 6 herein. In a preferred embodiment the xylanase is derived from *Aspergillus fumigatus*, such as the one shown in SEQ ID NO: 8 herein.

Contemplated xylanases also include those comprising an amino acid sequence having at least 60%, at least 70%, at least 80%, at least 85%, at least 90%, at least 95% identity, at least 97%, at least 98%, at least 99% identity to the *Aspergillus fumigatus* xylanase in WO 2006/078256 shown as SEQ ID NO: 8 herein, or the *Aspergillus aculeatus* xylanase disclosed in WO 94/21785 as SEQ ID NO: 5 (Xyl II) or SEQ ID NO: 6 herein.

Beta-xylosidases

In a preferred embodiment the hemicellulase used in a method or process of the invention is a beta-xylosidase, or the hemicellulolytic enzyme preparation comprises a beta-xylosidase. The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Examples of specifically contemplated beta-xylosidase includes the one derived from a strain of the genus *Aspergillus*, such as a strain of *Aspergillus fumigatus*, such as the one disclosed in WO 2013/028928 (Example 16 and 17), or derived from a strain of *Trichoderma*, such as a strain of *Trichoderma reesei*, such as the mature polypeptide of SEQ ID NO: 58 in WO 2011/057140.

The beta-xylosidase used during preconditioning may be comprised in a cellulolytic enzyme preparation. In one embodiment the hemicellulase is a cellulolytic enzyme preparation further comprising a beta-xylosidase, such as one derived from a strain of the genus *Aspergillus*, such as a strain of *Aspergillus fumigatus* (e.g., one disclosed in WO 2011/057140), such as one disclosed in WO 2013/028928 (Examples 16 and 17), or derived from a strain of *Trichoderma*, such as a strain of *Trichoderma reesei*, such as the mature polypeptide of SEQ ID NO: 58 in WO 2011/057140.

Contemplated beta-xylosidases also include those comprising an amino acid sequence having at least 60%, at least 70% at least 80%, at least 85%, at least 90%, at least 95% identity, at least 97%, at least 98%, at least 99% identity to the *Aspergillus fumigatus* beta-xylosidase disclosed as SEQ ID NO: 206 in WO 2011/057140 or SEQ ID NO: 9 herein or any of the beta-xylosidases mentioned herein.

The hemicellulase used for preconditioning is or may comprise a commercial hemicellulase product. Examples of commercial hemicellulase products include, for example, SHEARZYME™ (Novozymes A/S), CELLIC™ HTec (Novozymes A/S), CELLIC™ HTec2 (Novozymes A/S), CELLIC™ HTec3 (Novozymes), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Beta-Glucosidase

According to the invention a glucoamylase may be present or added during preconditioning or saccharification. Further, a cellulolytic enzyme preparation used according to the invention may in one embodiment comprise one or more beta-glucosidases. The beta-glucosidase may in one embodiment be one derived from a strain of the genus *Aspergillus*, such as *Aspergillus niger* or *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 5 herein or an *Aspergillus fumigatus* beta-glucosidase variant, such as one disclosed in WO 2012/044915, such as one with the following substitutions: F100D, S283G, N456E, F512Y.

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

In an embodiment beta-glucosidase is an *Aspergillus fumigatus* beta-glucosidase or homolog thereof selected from the group consisting of:
(i) a beta-glucosidase comprising the mature polypeptide of SEQ ID NO: 5 herein;
(ii) a beta-glucosidase comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 5 herein.

In an embodiment the beta-glucosidase is a variant comprises a substitution at one or more (several) positions corresponding to positions 100, 283, 456, and 512 of the mature polypeptide of SEQ ID NO: 5 herein, wherein the variant has beta-glucosidase activity.

In an embodiment the parent beta-glucosidase of the variant is (a) a polypeptide comprising the mature polypeptide of SEQ ID NO: 5 herein; (b) a polypeptide having at least 80% sequence identity to the mature polypeptide of SEQ ID NO: 5 herein or (c) a fragment of the mature polypeptide of SEQ ID NO: 5 herein, which has beta-glucosidase activity.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the amino acid sequence of the parent beta-glucosidase.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 5 herein.

In an embodiment the beta-glucosidase is from a strain of *Aspergillus*, such as a strain of *Aspergillus fumigatus*, such as *Aspergillus fumigatus* beta-glucosidase (SEQ ID NO: 5 herein), which comprises one or more substitutions selected from the group consisting of L89M, G91L, F100D, I140V, I186V, S283G, N456E, and F512Y; such as a variant thereof with the following substitutions:
F100D+S283G+N456E+F512Y;
L89M+G91L+I186V+I140V;
I186V+L89M+G91L+I140V+F100D+S283G+N456E+F512Y.

In an embodiment the number of substitutions is between 1 and 10, such 1 and 8, such as 1 and 6, such as 1 and 4, such as 1, 2, 3, 4, 5, 6, 7, 8, 9 or 10 substitutions.

In an embodiment the variant comprises a substitution at a position corresponding to position 100, a substitution at a position corresponding to position 283, a substitution at a position corresponding to position 456, and/or a substitution at a position corresponding to position 512.

In a preferred embodiment the beta-glucosidase variant comprises the following substitutions: Phe100Asp, Ser283Gly, Asn456Glu, Phe512Tyr in SEQ ID NO: 5 herein.

GH61 Polypeptide Having Cellulolytic Enhancing Activity

The cellulolytic enzyme preparation used according to the invention may in one embodiment comprise one or more GH61 polypeptide having cellulolytic enhancing activity. In one embodiment the enzyme composition comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2 or SEQ ID NO: 4 herein; or one derived from the genus *Thielavia*, such as a strain of *Thielavia terrestris*, such as the one described in WO 2005/074647 as SEQ ID NO: 7 and SEQ ID NO: 8 and SEQ ID NO: 2 herein; or one derived from a strain of *Aspergillus*, such as a strain of *Aspergillus fumigatus*, such as the one described in WO 2010/138754 as SEQ ID NO: 2; or one derived from a strain derived from *Penicillium*, such as a strain of *Penicillium emersonii*, such as the one disclosed in WO 2011/041397 or SEQ ID NO: 7 herein.

In an embodiment the *Penicillium* sp. GH61 polypeptide having cellulolytic enhancing activity or homolog thereof is selected from the group consisting of:
(i) a GH61 polypeptide having cellulolytic enhancing activity comprising the mature polypeptide of SEQ ID NO: 7 herein;
(ii) a GH61 polypeptide having cellulolytic enhancing activity comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 7 herein.

Cellobiohydrolase I

The cellulolytic enzyme preparation used according to the invention may in one embodiment may comprise one or more CBH I (cellobiohydrolase I). In one embodiment the cellulolytic composition comprises a cellobiohydrolase I (CBH I), such as one derived from a strain of the genus *Aspergillus*, such as a strain of *Aspergillus fumigatus*, such as the Cel7A CBHI disclosed in SEQ ID NO: 6 in WO 2011/057140 or SEQ ID NO: 10 herein, or a strain of the genus *Trichoderma*, such as a strain of *Trichoderma reesei*.

In an embodiment the *Aspergillus fumigatus* cellobiohydrolase I or homolog thereof is selected from the group consisting of:
(i) a cellobiohydrolase I comprising the mature polypeptide of SEQ ID NO: 10 herein;
(ii) a cellobiohydrolase I comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 10 herein.

Cellobiohydrolase II

The cellulolytic enzyme preparation used according to the invention may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, such as the one in SEQ ID NO: 11 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the *Aspergillus fumigatus* cellobiohydrolase II or homolog thereof is selected from the group consisting of:
(i) a cellobiohydrolase II comprising the mature polypeptide of SEQ ID NO: 11 herein;
(ii) a cellobiohydrolase II comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 11 herein.

Endoglucanase

The term "endoglucanase" means an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Cellulolytic Enzyme Preparation

According to the invention a cellulolytic enzyme preparation is present or added during saccharification. A cellulolytic enzyme preparation is a preparation containing one or more (e.g., several) enzymes that hydrolyze cellulosic material. Such enzymes include endoglucanase, cellobiohydrolase, beta-glucosidase, or combinations thereof.

The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity for, e.g., a cellulolytic enzyme preparation, may be determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., 60° C., or 65° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., 60° C., or 65° C., 72 hours, sugar analysis by AMINEX® HPX-87H column (Bio-Rad Laboratories, Inc., Hercules, Calif., USA).

As mentioned above a cellulolytic enzyme preparation used for saccharification (hydrolysis) in a process of the invention typically comprises one or more endoglucanases, cellobiohydrolases and/or beta-glucosidases.

In an embodiment the cellulolytic enzyme preparation is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme preparation is derived from a strain of *Trichoderma reesei*.

The cellulolytic enzyme preparation may further comprise one or more of the following polypeptides, such as enzymes: GH61 polypeptide having cellulolytic enhancing activity, beta-glucosidase, xylanase, beta-xylosidase, CBHI, CBHII, or a mixture of two, three, four, five or six thereof.

The further polypeptide(s) (e.g., GH61 polypeptide) and/or enzyme(s) (e.g., beta-glucosidase, xylanase, beta-xylosidase, CBH I and/or CBH II may be foreign to the cellulolytic enzyme preparation producing organism (e.g., *Trichoderma reesei*).

In an embodiment the cellulolytic enzyme preparation comprises a GH61 polypeptide having cellulolytic enhancing activity and a beta-glucosidase.

In another embodiment the cellulolytic enzyme preparation comprises a GH61 polypeptide having cellulolytic enhancing activity, a beta-glucosidase, and a CBHI.

In another embodiment the cellulolytic enzyme preparation comprises a GH61 polypeptide having cellulolytic enhancing activity, a beta-glucosidase, a CBHI and a CBHII.

Other enzymes, such as endoglucanases, may also be comprises in the cellulolytic enzyme preparation.

As mentioned above the cellulolytic enzyme preparation may comprise a number of difference polypeptides, including enzymes.

In an embodiment the cellulolytic enzyme preparation comprises a *Trichoderma reesei* cellulolytic preparation, further comprising *Thermoascus aurantiacus* GH61A polypeptide having cellulolytic enhancing activity (e.g., WO 2005/074656), and *Aspergillus oryzae* beta-glucosidase fusion protein (e.g., WO 2008/057637).

In another embodiment the cellulolytic enzyme preparation comprises a *Trichoderma reesei* cellulolytic enzyme preparation, further comprising *Thermoascus aurantiacus* GH61A polypeptide having cellulolytic enhancing activity (SEQ ID NO: 2 in WO 2005/074656 or SEQ ID NO: 4 herein), and *Aspergillus fumigatus* beta-glucosidase (SEQ ID NO: 2 of WO 2005/047499 or SEQ ID NO: 5 herein).

In another embodiment the cellulolytic enzyme preparation comprises a *Trichoderma reesei* cellulolytic enzyme preparation further comprising *Penicillium emersonii* GH61A polypeptide having cellulolytic enhancing activity disclosed in WO 2011/041397 or SEQ ID NO: 7 herein, and *Aspergillus fumigatus* beta-glucosidase (SEQ ID NO: 2 of WO 2005/047499 or SEQ ID NO: 5 herein).

In another embodiment the cellulolytic enzyme preparation comprises a *Trichoderma reesei* cellulolytic enzyme preparation further comprising *Penicillium emersonii* GH61A polypeptide having cellulolytic enhancing activity disclosed in WO 2011/041397, and *Aspergillus fumigatus* beta-glucosidase (SEQ ID NO: 2 of WO 2005/047499) or variant disclosed in WO 2012/044915 (hereby incorporated by reference), the following substitutions: F100D, S283G, N456E, F512Y.

In an embodiment the cellulolytic enzyme preparation is derived from *Trichoderma reesei* further comprising a GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140 or SEQ ID NO: 11 herein.

In a preferred embodiment the cellulolytic enzyme preparation from *Trichoderma reesei*, further comprises a hemicellulase or hemicellulolytic enzyme preparation, such as an *Aspergillus fumigatus* xylanase (e.g. SEQ ID NO: 8 herein) and *Aspergillus fumigatus* beta-xylosidase (e.g. SEQ ID NO: 9 herein).

In an embodiment the cellulolytic enzyme preparation also comprises a xylanase (e.g., derived from *Aspergillus aculeatus* or *Aspergillus fumigatus*) and/or a beta-xylosidase (e.g., derived from *Aspergillus fumigatus*).

In another embodiment the cellulolytic enzyme preparation comprises a *Trichoderma reesei* cellulolytic preparation, further comprising *Thermoascus aurantiacus* GH61A polypeptide having cellulolytic enhancing activity (WO 2005/074656), *Aspergillus oryzae* beta-glucosidase fusion protein (WO 2008/057637), and *Aspergillus aculeatus* xylanase (Xyl II in WO 94/21785).

In another embodiment the cellulolytic enzyme preparation comprises a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785 or SEQ ID NO: 6 herein).

In another embodiment the cellulolytic enzyme preparation comprises a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785 or SEQ ID NO: 6 herein).

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) and *Aspergillus fumigatus* xylanase (Xyl III in WO 2006/078256).

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499), *Aspergillus fumigatus* xylanase (Xyl III in WO 2006/078256), and Cel7A CBH I from *Aspergillus fumigatus* disclosed as SEQ ID NO: 2 in WO 2011/057140.

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499), *Aspergillus fumigatus* xylanase (Xyl III in WO 2006/078256), Cel7A CBH I from *Aspergillus fumigatus* disclosed as SEQ ID NO: 2 in WO 2011/057140, and CBH II derived from *Aspergillus fumigatus* disclosed in WO 2013/028928.

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) or variant with the following substitutions: F100D, S283G, N456E, F512Y; *Aspergillus fumigatus* xylanase (Xyl III in WO 2006/078256), Cel7A CBH I from *Aspergillus fumigatus* disclosed as SEQ ID NO: 2 in WO 2011/057140, and CBH II derived from *Aspergillus fumigatus* disclosed in WO 2013/028928.

All cellulolytic enzyme preparations disclosed in WO 2013/028928 are also contemplated and hereby incorporated by reference.

The cellulolytic enzyme preparation comprises or may further comprise one or more (several) proteins selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

In an embodiment the cellulolytic enzyme preparation is or comprises a commercial cellulolytic enzyme preparation.

Examples of commercial cellulolytic enzyme preparations suitable for use in the present invention include, for example, CELLIC™ CTec (Novozymes A/S), CELLIC™ Ctec2 (Novozymes A/S), CELLIC™ Ctec3 (Novozymes A/S), CELLUCLAST™ (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.).

The cellulolytic enzyme preparation may be present or added during saccharification in amounts effective from about 0.001 to about 5.0 wt % of solids (TS), more preferably from about 0.025 to about 4.0 wt % of solids, and most preferably from about 0.005 to about 2.0 wt % of solids (TS).

The present invention is further described by the following examples that should not be construed as limiting the scope of the invention.

Material & Methods

Materials:

Laccase A ("L"): Laccase derived from *Myceliophthora thermophila* (MtL) disclosed in WO 95/33836 and available from Novozymes NS, Denmark.

Cellulolytic Enzyme Preparation C3 ("C3"): Cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140 and SEQ ID NO: 11 herein. Further, Cellulolytic Enzyme Preparation C3 further comprises 10% Hemicellulolytic Enzyme Preparation H3.

Hemicellulolytic Enzyme Preparation H3 ("H3"): Cellulolytic enzyme preparation from *Trichoderma reesei*, further comprising *Aspergillus fumigatus* xylanase (SEQ ID NO: 8 herein) and *Aspergillus fumigatus* beta-xylosidase (SEQ ID NO: 9 herein).

Glucoamylase GA ("GA"): Glucoamylase derived from *Aspergillus niger* shown in SEQ ID NO: 13 herein.

Glucoamylase preparation 188 ("GA188"): *Aspergillus niger* enzyme preparation comprising 57% glucoamylase, 27% beta-glucosidase and 16% alpha-amylase (protein content basis).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1

Effect of Preconditioning on Oil Extraction/Recovery and Glucose Yield after Saccharification Low severity dilute acid pretreated (160° C., 3% $H_2SO_4$ (w/w) for 5 minutes) dry fraction corn fiber was preconditioned at about 23% TS (Total Solids) at 50° C. for 6 hours in a kettle reactor with high mixing with:

0.015 mg Laccase A/g cellulose;
0.2 mg Hemicellulolytic Enzyme Preparation H3/g cellulose;
0.114 mg Glucoamylase GA/g cellulose;
0.2 mg Glucoamylase Preparation 188/g cellulose).
No Preconditioning (Control)

After preconditioning, 1.8 mg Cellulolytic Enzyme Preparation C3/g cellulose was added and hydrolysis was carried out at 20% TS at 50° C. for 5 days. After 5 days hydrolysis, 25 grams of the whole slurry hydrolysate was added into a 50 ml tube, and then 3.13 mL of 95% n-Hexane (Fisher Scientific) was added. The hydrolysate/n-hexane mixture was mixed well and then centrifuged on 3000 G in a floor centrifuge (Thermo Scientific, Legeng RT+ centrigure) for 10 minutes. After centrifugation, the top layer was transferred into a 3 mL tube by positive displacement pipettes. The weight of transferred liquor was measured. The oil content and density was measured using a densitometer and recorded. The oil was extracted from the hydrolysate again and all data were recorded and the final extracted oil was calculated as: Extracted oil=(first extracted oil+second extracted oil) (g)/total dry hydrolysate (g) and the results are shown in FIG. 1.

Figure 2:
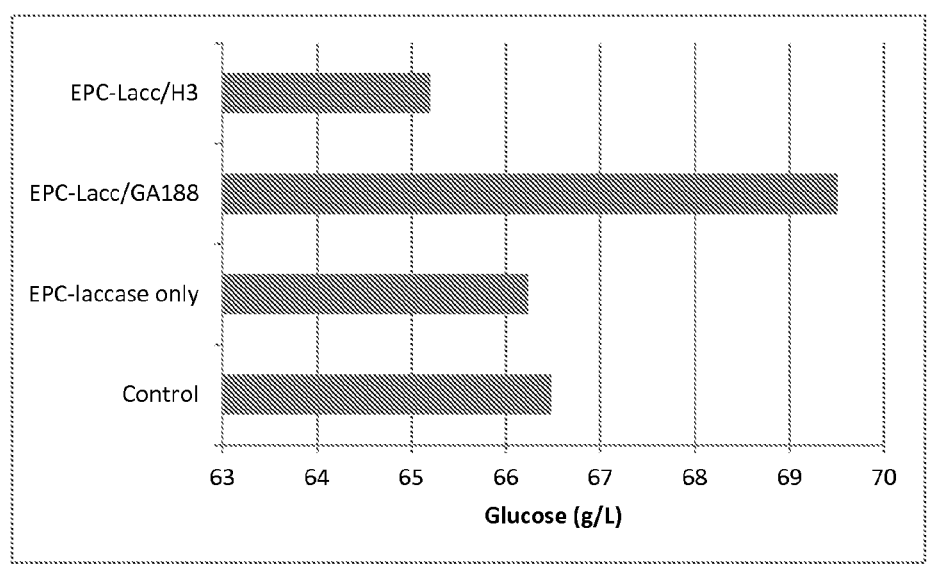
FIG. 2 shows the effect of enzymatic preconditioning on the glucose yield in corn fiber hydrolysate:
Control: saccharification with Cellulolytic Enzyme Preparation C3;
EPC-Laccase only: preconditioned with Laccase A only and then hydrolyzed with Cellulolytic Enzyme Preparation C3;
EPC-Lacc H3: preconditioned with Laccase A and Hemicellulolytic Enzyme Preparation H3 and then hydrolyzed with Cellulolytic Enzyme Preparation C3;
EPC-Lacc/GA188: preconditioned with Laccase A and Glucoamylase 188 and then hydrolyzed with Cellulolytic Enzyme Preparation C3.

The glucose yield was determined using HPLC with Aminex HPX-87H column. The results are shown in FIG. 2.

Example 2

Effect of Precondition on Glucose Yield after Saccharification

Example 1 was repeated, except that the dry fraction corn fiber during preconditioning was about 17% TS. Preconditioning was done with 0.015 mg Laccase A/g cellulose and 0.114 mg Glucoamylase GA followed by saccharification with 2.0 mg Cellulolytic Enzyme Preparation C3. As control the process was repeating without preconditioning.

Figure 3:
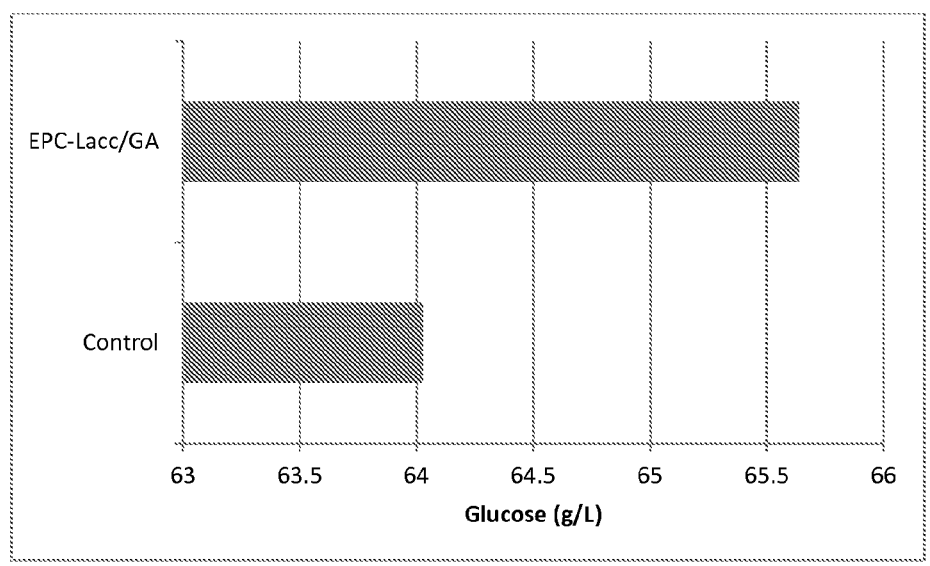
FIG. 3 shows the effect of enzymatic preconditioning on the glucose yield in corn fiber hydrolysate:
Control: saccharification with Cellulolytic Enzyme Preparation C3;
EPC-Lacc/GA: preconditioned with Laccase A and Glucoamylase GA and then saccharified with Cellulolytic Enzyme Preparation C3.

The glucose yield was determined. The results are shown in FIG. 3.

The invention claimed is:

1. A process of recovering oil from pretreated cellulosic material comprising the steps of:
preconditioning the pretreated cellulosic material with a phenol oxidizing enzyme and a glucoamylase;
(ii) saccharifying the preconditioned material with a cellulolytic enzyme preparation;
(iii) recovering oil from saccharified material in step (ii).

2. A process of producing a sugar from pretreated cellulosic material comprising the steps of:
preconditioning the pretreated cellulosic material with a phenol oxidizing enzyme and a glucoamylase;
(ii) saccharifying the preconditioned material with a cellulolytic enzyme preparation; and
(iii) recovering oil from saccharified material in step (ii).

3. The process of claim 2, wherein the phenol oxidizing enzyme is a laccase.

4. The process of claim 2, further comprising recovering sugars from the saccharified material from step (ii).

5. The process of claim 2, wherein the glucoamylase is derived from a strain of Aspergillus.

6. The process of claim 2, wherein the preconditioning further comprises addition of beta-glucosidase, alpha amylase, hemicellulase or combination thereof.

7. The process of claim 2, wherein the pretreated cellulosic material is dilute acid pretreated or auto-hydrolyzed.

8. The process of claim 2, wherein the pretreated cellulosic material is unwashed, un-detoxified or washed.

9. The process of claim 2, wherein the sugar produced is increased as compared to when no preconditioning is done.

10. The process of claim 2, wherein the oil is recovered and an increased amount of oil is released compared to when no preconditioning is done.

11. The process of claim 2, wherein the glucoamylase is derived from a strain of Aspergillus niger or Aspergillus oryzae.

12. The process of claim 2, wherein the glucoamylase comprises a polypeptide having the sequence of SEQ ID NO: 13.

* * * * *